(12) United States Patent  (10) Patent No.: US 7,294,591 B2
Soerens et al.  (45) Date of Patent: *Nov. 13, 2007

(54) ABSORBENT COMPOSITE INCLUDING A FOLDED SUBSTRATE AND AN ABSORBENT ADHESIVE COMPOSITION

(75) Inventors: Dave Allen Soerens, Neenah, WI (US); Cathleen Mae Uttecht, Menasha, WI (US); Hoa La Wilhelm, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 660 days.

This patent is subject to a terminal disclaimer.

(21) Appl. No.: 10/318,567

(22) Filed: Dec. 13, 2002

(65) Prior Publication Data

US 2004/0116014 A1 Jun. 17, 2004

(51) Int. Cl.
*B32B 3/00* (2006.01)
*B32B 5/02* (2006.01)
(52) U.S. Cl. .................. 442/59; 442/97; 442/99
(58) Field of Classification Search ........... 442/118, 442/59, 97, 99; 604/365, 385.01; 428/40.1
See application file for complete search history.

(56) References Cited

U.S. PATENT DOCUMENTS

| | | |
|---|---|---|
| 3,595,235 A | 7/1971 | Jespersen |
| 3,617,362 A | 11/1971 | Bemmels et al. |
| 3,699,966 A | 10/1972 | Chapuis |
| 3,729,005 A * | 4/1973 | Lee et al. .................. 604/366 |
| 3,855,046 A | 12/1974 | Hansen et al. |
| 3,897,784 A | 8/1975 | Fitzgerald |
| 3,951,893 A * | 4/1976 | Gander .................. 524/322 |
| 3,959,569 A | 5/1976 | Burkholder, Jr. |
| 3,963,605 A | 6/1976 | Seabourn |
| 3,968,798 A | 7/1976 | Hokanson |
| 4,217,900 A | 8/1980 | Wiegner et al. |
| 4,232,674 A | 11/1980 | Melican |
| 4,251,643 A | 2/1981 | Harada et al. |
| 4,291,136 A | 9/1981 | Keogh |
| 4,317,449 A | 3/1982 | Nowakoski |
| 4,328,323 A | 5/1982 | Keogh |
| 4,333,465 A | 6/1982 | Wiegner |
| 4,343,917 A | 8/1982 | Keogh |
| 4,353,997 A | 10/1982 | Keogh |
| 4,369,289 A | 1/1983 | Keogh |
| 4,381,782 A | 5/1983 | Mazurak et al. |
| 4,408,011 A | 10/1983 | Barnabeo |
| 4,410,324 A | 10/1983 | Sabee |
| 4,434,272 A | 2/1984 | Keogh |
| 4,440,907 A | 4/1984 | Keogh |
| 4,446,279 A | 5/1984 | Keogh |

(Continued)

FOREIGN PATENT DOCUMENTS

CA 756190 4/1967

(Continued)

*Primary Examiner*—Terrel Morris
*Assistant Examiner*—Matthew D. Matzek
(74) *Attorney, Agent, or Firm*—Pauley Petersen & Erickson

(57) ABSTRACT

An absorbent composite is provided including a substrate, at least a portion of which is coated with an absorbent adhesive composition. The substrate is folded upon itself to provide a plurality of panels. A personal care product including the absorbent composite is also disclosed.

49 Claims, 12 Drawing Sheets

U.S. PATENT DOCUMENTS

| | | | |
|---|---|---|---|
| 4,459,396 A | 7/1984 | Yamasaki et al. | |
| 4,489,029 A | 12/1984 | Keogh et al. | |
| 4,493,924 A | 1/1985 | Rifi | |
| 4,526,930 A | 7/1985 | Keogh | |
| 4,551,504 A | 11/1985 | Barnabeo | |
| 4,575,535 A | 3/1986 | Keogh | |
| 4,576,596 A | 3/1986 | Jackson et al. | |
| 4,578,070 A | 3/1986 | Holtman | |
| 4,579,913 A | 4/1986 | Keogh | |
| 4,585,449 A | 4/1986 | Karami | |
| 4,593,071 A | 6/1986 | Keogh | |
| 4,676,784 A | 6/1987 | Erdman et al. | |
| 4,676,820 A | 6/1987 | Le Sergent et al. | |
| 4,753,993 A | 6/1988 | Keogh | |
| 4,921,136 A | 5/1990 | Roggenburg, Jr. | |
| 4,940,646 A | 7/1990 | Pawlowski | |
| 4,960,477 A | 10/1990 | Mesek | |
| 5,035,892 A | 7/1991 | Blank et al. | |
| 5,047,476 A | 9/1991 | Keogh | |
| 5,072,687 A | 12/1991 | Mitchell et al. | |
| 5,089,564 A | 2/1992 | Bullen | |
| 5,112,919 A | 5/1992 | Furrer et al. | |
| 5,145,906 A | 9/1992 | Chambers et al. | |
| 5,196,470 A | 3/1993 | Anderson et al. | |
| 5,204,404 A | 4/1993 | Werner, Jr. et al. | |
| 5,364,382 A | 11/1994 | Latimer et al. | |
| 5,389,728 A | 2/1995 | Prejean | |
| 5,423,786 A | 6/1995 | Fung et al. | |
| 5,429,788 A | 7/1995 | Ribble et al. | |
| 5,532,350 A | 7/1996 | Cottrell et al. | |
| 5,538,783 A | 7/1996 | Hansen et al. | |
| 5,558,832 A | 9/1996 | Noel et al. | |
| 5,614,570 A | 3/1997 | Hansen et al. | |
| 5,635,191 A | 6/1997 | Roe et al. | |
| 5,637,106 A | 6/1997 | Mitchell et al. | |
| 5,643,237 A * | 7/1997 | Fechillas et al. | 604/366 |
| 5,643,588 A | 7/1997 | Roe et al. | |
| 5,656,132 A | 8/1997 | Farrington, Jr. et al. | |
| 5,730,737 A | 3/1998 | Widlund et al. | |
| 5,807,364 A * | 9/1998 | Hansen | 604/367 |
| 5,814,567 A | 9/1998 | Yahiaoui et al. | |
| 5,827,254 A | 10/1998 | Trombetta et al. | |
| 5,853,867 A | 12/1998 | Harada et al. | |
| 5,879,751 A | 3/1999 | Bogdanksi | |
| 5,885,266 A | 3/1999 | Chihani et al. | |
| 5,932,068 A | 8/1999 | Farrington, Jr. et al. | |
| 5,932,668 A | 8/1999 | Friebe et al. | |
| 5,964,742 A | 10/1999 | McCormack et al. | |
| 6,020,071 A | 2/2000 | Watson | |
| 6,051,317 A | 4/2000 | Brueggemann et al. | |
| 6,054,523 A | 4/2000 | Braun et al. | |
| 6,060,636 A | 5/2000 | Yahiaoui et al. | |
| 6,159,591 A | 12/2000 | Beihoffer et al. | |
| 6,222,091 B1 | 4/2001 | Beihoffer et al. | |
| 6,235,965 B1 | 5/2001 | Beihoffer et al. | |
| H1969 H | 6/2001 | Fell et al. | |
| 6,329,565 B1 | 12/2001 | Dutkiewicz et al. | |
| H2011 H | 1/2002 | Freiburger et al. | |
| 6,342,298 B1 | 1/2002 | Evans et al. | |
| 6,376,072 B1 | 4/2002 | Evans et al. | |
| 6,403,857 B1 | 6/2002 | Gross et al. | |
| 6,417,425 B1 | 7/2002 | Whitmore et al. | |
| 6,596,402 B2 | 7/2003 | Soerens et al. | |
| 6,610,793 B1 * | 8/2003 | Soerens et al. | 525/404 |
| 6,737,491 B2 | 5/2004 | Soerens et al. | |
| 6,808,801 B2 | 10/2004 | George et al. | |
| 6,822,135 B2 | 11/2004 | Soerens et al. | |
| 6,849,685 B2 | 2/2005 | Soerens et al. | |
| 6,887,961 B2 | 5/2005 | Soerens et al. | |
| 6,964,803 B2 | 11/2005 | Krautkramer et al. | |
| 2002/0090453 A1 | 7/2002 | Muthiah et al. | |
| 2003/0149413 A1 | 8/2003 | Mehawej | |
| 2004/0043688 A1 | 3/2004 | Soerens et al. | |
| 2004/0106721 A1 | 6/2004 | Soerens | |

FOREIGN PATENT DOCUMENTS

| | | |
|---|---|---|
| EP | 0 506 336 A1 | 9/1992 |
| EP | 0 649 644 A1 | 4/1995 |
| EP | 748 894 | 12/1996 |
| EP | 0 829 245 A2 | 3/1998 |
| EP | 923 921 | 6/1999 |
| EP | 947 549 | 10/1999 |
| EP | 1 013 291 | 6/2000 |
| EP | 1 050 612 | 11/2000 |
| EP | 0 992 252 A2 | 12/2000 |
| EP | 1 110 525 A1 | 6/2001 |
| EP | 1 199 059 A1 | 4/2002 |
| WO | 99/49826 | 10/1999 |
| WO | 99/57201 | 11/1999 |
| WO | 00/36199 | 6/2000 |
| WO | 00/47153 | 8/2000 |
| WO | 01/05440 | 1/2001 |
| WO | 01/26593 | 4/2001 |
| WO | 01/26596 | 4/2001 |
| WO | 01/34082 | 5/2001 |

* cited by examiner

ABSORBENT COMPOSITE INCLUDING A FOLDED SUBSTRATE AND AN ABSORBENT ADHESIVE COMPOSITION

FIELD OF INVENTION

The present invention relates to a substrate, at least a portion of which is coated with an absorbent adhesive composition, that is folded to provide an absorbent composite.

BACKGROUND OF THE INVENTION

Personal care products typically include an absorbent layer and a number of non-absorbent structural layers to enhance the functionality of the absorbent layer. The primary function of the absorbent layer is to absorb fluids. The absorbent layer is also required to provide functions such as, for example, intake, distribution and retention in order to effectively inhibit and/or prevent leakage of body fluids and solid exudates from the product.

In order to meet these needs, designers of personal care products have developed absorbent assemblies that typically include one or more layers of material, each designed to deliver a specific function. For example, surge layers are often included to rapidly take in fluid to prevent overwhelming the absorbent layer at the point of insult, particularly in the presence of large urine insults. Other materials such as wicking layers or barrier layers are added to assist in distributing fluid and preventing leakage. Superabsorbent materials are typically combined with other absorbent materials such as cellulosic fibers or fluff to retain absorbed fluids within the absorbent assembly. Additionally, layers of moisture-insensitive adhesives are provided to hold these layers together. These layered absorbent assemblies are generally bulky and do not conform well to the anatomy of the wearer. Furthermore, dislocation of the separate layers with respect to each other due to the wearer's movement during use can result in poor fluid management. As a result, personal care products including such layered absorbent assemblies may not perform as intended, may have poor fit and may result in discomfort during use.

Another potential shortfall of these layered absorbent assemblies is the complex and inefficient processes needed to produce them. Generally, each layer must be produced offline using a specific technology and then individually fed into the manufacturing process. The combined layers are then typically cut to the desired shape resulting in waste and cost inefficiencies.

Personal care product designers have attempted to address various aspects of these problems in a variety of ways. For example, it is known to fold an absorbent composite to provide channels or depressions to receive, distribute and retain body fluids and solid exudates. It is also known to fold an absorbent composite to provide bulk in the central or side portions of the absorbent composite to prevent deformation of the absorbent composite in use and to assist in distributing or directing fluids. Others have utilized designs that reduce waste by cutting an absorbent composite to a particular shape and folding the cut portions into the center or crotch portion of the assembly to provide additional absorbent capacity. In each case the folding of the absorbent composite results in greater bulk in the target area (e.g. the crotch or central region and/or side margins). However, for the purposes of discretion and comfort it is desirable to have as thin an absorbent composite as possible without sacrificing absorbent capacity.

Despite all of these techniques there is still a need for an absorbent core that is thin, durable, structurally stable and performs multiple functions. There is also a need for an absorbent composite wherein the layers maintain proper position with respect to adjacent layers. Additionally, there is also a need to reduce the bulk of and/or eliminate some of the non-absorbent structural layers to provide a personal care product having a desired level of fit, comfort and performance that is more efficient and less expensive to produce.

SUMMARY OF THE INVENTION

In response to all of the discussed difficulties and problems encountered in the prior art, a new absorbent composite that provides several of the desired fluid handling functions within a single absorbent composite has been developed. This capability eliminates the need to include additional performance enhancing layers such as surge or wicking layers that add bulk to personal care products.

The absorbent composite includes a substrate, at least a portion of which is coated with an absorbent adhesive composition, which is folded to form a plurality of panels. The substrate may be a single sheet of material wherein each panel performs a different fluid handling function. The substrate may optionally be treated with a fluid and/or menses modifying material or an odor control agent. The substrate is coated with the absorbent adhesive composition using a variety of application patterns and techniques. The absorbent adhesive composition may be an absorbent binder or an absorbent in situ neutralizable binder composition and may optionally include a superabsorbent material, a fluid modifying material and/or an odor control agent. The substrate is folded to provide an absorbent composite having one of a variety of suitable cross-sectional configurations that contribute to the overall functionality of the absorbent composite. Desirably, the substrate is folded such that the absorbent adhesive composition is enclosed within the absorbent composite. Suitably, the absorbent composite may be relatively thin and flexible.

The absorbent composite may be used to make personal care products such as, for example, diapers, diaper pants, training pants, feminine hygiene products, incontinence products, swimwear garments, bed mats, tissue, wipes, medical articles and the like. For example, an absorbent garment may include an absorbent composite. Alternatively, an absorbent composite may be used to form an absorbent garment wherein the absorbent composite includes a substrate, at least a portion of which is coated with an absorbent adhesive composition, which is folded to form at least a portion of an outer cover of the garment. Additionally, an absorbent composite may be used to form a feminine hygiene product. For example, a feminine hygiene product may include an absorbent composite as described above, a garment attachment adhesive and release strip.

With the foregoing in mind, it is a feature and advantage of the invention to provide a thin, durable, structurally stable, and multifunctional absorbent composite. It is a further feature and advantage of the invention to provide a personal care product that is thinner, more efficient and less expensive to manufacture compared to conventional personal care products.

BRIEF DESCRIPTION OF THE DRAWINGS

These and other objects and features of this invention will be better understood from the following detailed description taken in conjunction with the drawings, wherein.

DEFINITIONS

Figure 1:
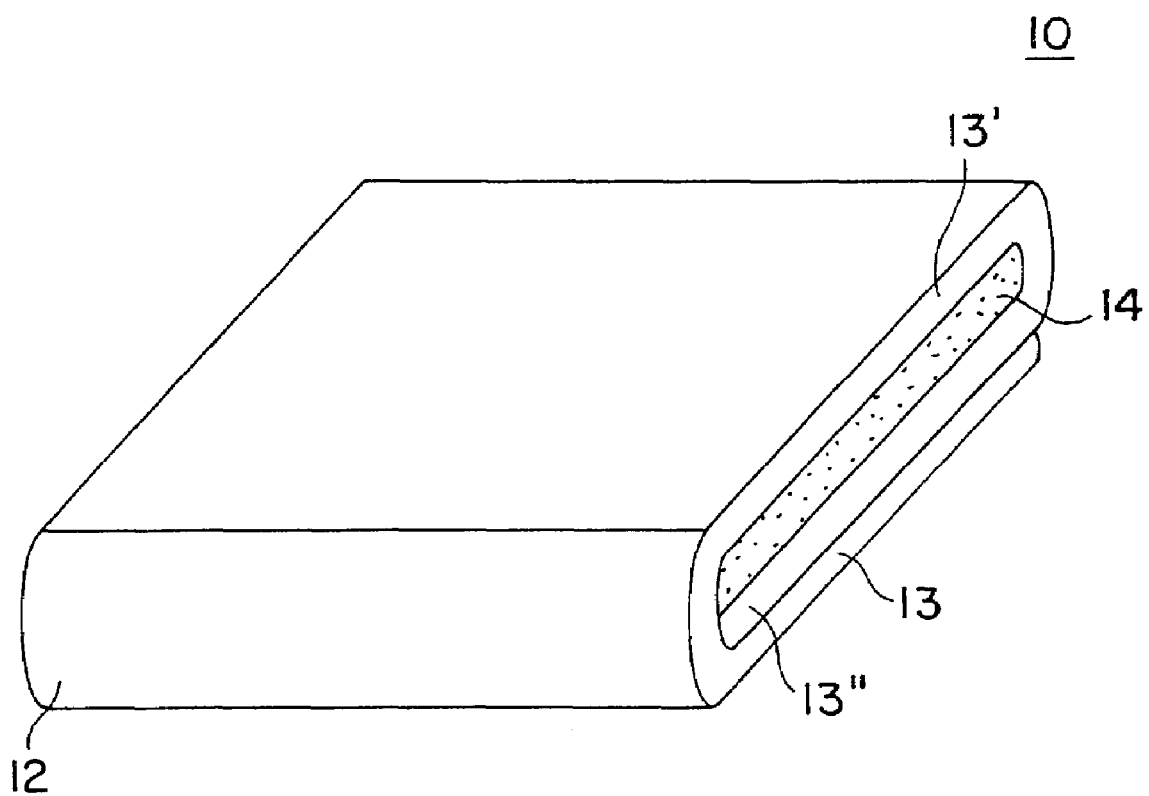
FIG. 1 illustrates a representative absorbent composite of the present invention.

Within the context of this specification, each term or phrase below will include the following meaning or meanings.

"Barrier function" refers to a fluid handling function wherein a substrate assists in preventing the strikethrough of absorbed fluids.

"Binder" refers to a material having binding, adhesive or attachment properties with or without chemical, thermal, pressure or other treatment.

"Body contact" refers to a fluid handling function that results from providing a liquid-permeable substrate on a body-facing surface of an absorbent composite that promotes fluid transfer to absorbent components and may inhibit flowback of fluid to the body-facing surface from the absorbent components.

"Cross-sectional profile" refers to a profile created by a plane cutting an absorbent composite perpendicular to at least one foldline.

"Desalination" refers to a fluid handling function wherein an electrolyte capable of binding sodium ions is brought in to close contact with an electrolyte capable of binding chloride ions to reduce the local saline concentration and enhance fluid absorption.

"Distribution" refers to a fluid handling function wherein a fluid is dispersed, wicked, spread, directed or the like within an absorbent composite.

"Feminine hygiene products" include sanitary pads and napkins, as well as tampons and interlabial feminine hygiene products.

"Fluid handling function" refers to an attribute of an absorbent composite that assists in the collection, transport and/or absorption of fluids. Such fluid handling functions include, but are not limited to, barrier function, body contact, desalination, distribution, feces containment, feces modification, intake, lock-up, menses containment, menses modification, odor control, retention, and skin treatment.

"Fluid modifying material" includes, but is not limited to, surfactants that change or modify a physical or chemical property of a body exudates such as urine, feces or menses.

"Intake" refers to a fluid handling function wherein a substrate is capable of rapidly capturing a fluid insulted upon an absorbent composite.

"Layer", as used herein, includes, but is not limited to, single unfolded sheets of material, folded sheets of material, strips of material, loose or bonded fibers, multiple sheets or laminates of materials, or other combinations of such materials.

"Lock-up" refers to a fluid handling function wherein a fluid is held within a material and may not be easily given up under pressure.

"Modifying agent" refers to a substance that may be added to a substrate to modify a physical property of a fluid, such as the viscosity of the fluid, or to affect the fluid permeability of the substrate.

"Multi-functional" refers to a material that may perform two or more fluid handling functions.

"Nonwoven" or "nonwoven web" refers to materials and webs or material having a structure of individual fibers or filaments which are interlaid, but not in an identifiable manner as in a knitted fabric. The terms "fiber" and "filament" are used interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Panel", as used herein, includes, but is not limited to, a region or section of a layer wherein at least a portion of the periphery of the region or section is adjacent a foldline.

"Personal care product" includes diapers, diaper pants, training pants, swim wear, absorbent underpants, adult incontinence products, feminine hygiene products, and the like.

"Plurality" means two or more elements or parts such as, for example, an absorbent composite including two or more panels.

"Retention" refers to capacity, storage, containment or similar fluid handling function.

"Shape" or "shaping" refers to cutting, heating, molding or similar process used to impart a desired 2- or 3-dimensional configuration to an absorbent composite.

"Structurally stable" refers to a material capable of maintaining various elements, layers or components of an absorbent core in position with respect to each other.

"Substrate" refers to a material having a basis weight of about 150 grams per square meter or less, a fluid centrifuge retention capacity of about 10 grams fluid per gram material or less, and a peak tensile strength under load of at least about 50 grams per centimeter width.

"Superabsorbent" refers to a water-swellable, water-insoluble organic or inorganic material capable, under the most favorable conditions, of absorbing at least about 15 times its weight and, desirably, at least about 25 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers.

These terms may be defined with additional language in the remaining portions of the specification.

DESCRIPTION OF PREFERRED EMBODIMENTS

The present invention is directed to an absorbent composite including a substrate, at least a portion of which is coated with an absorbent adhesive composition, which is folded to provide a plurality of panels. Each panel may provide a different fluid handling function. The fluid handling functions may be selected from barrier function, body contact, desalination, distribution, feces containment, feces modification, intake, lock-up, menses containment, menses modification, odor control, retention or skin treatment.

Suitably, the absorbent composite has an absorbent capacity of at least about 5 grams 0.9 weight percent saline per gram composite, alternatively at least about 10 grams 0.9 weight percent saline per gram composite. Desirably, the absorbent composite is relatively dense and thus may have a density of at least about 0.5 grams per cubic centimeter, or at least about 0.7 grams per cubic centimeter. Advantageously, the absorbent composite is relatively flexible in order to conform more closely to a wearer's body and inhibit and/or prevent leakage when included in a personal care product. Therefore, the absorbent composite may have a Gurley stiffness value of about 320 milligrams or less, especially about 160 milligrams or less. Preferably, the absorbent composite is also relatively thin in order to provide better fit and comfort when included in a personal care product. Therefore, the folded absorbent composite may have a thickness of about 0.2 to about 4 millimeters.

Referring to FIG. 1, an absorbent composite 10 includes a substrate 12, at least a portion of which is coated with an adhesive composition 14. The substrate 12 is folded upon itself to form an absorbent composite having a plurality of panels 13. For example, as shown in FIG. 1, the absorbent composite includes three panels, 13, 13' and 13" respectively.

Desirably, the substrate 12 is a single sheet or layer of material that may be configured to provide one or more desired fluid handling functions such as, but not limited to, barrier function, body contact, distribution, feces containment, feces modification, intake, lock-up, menses containment, menses modification, odor control, retention, and skin treatment.

The substrate 12 may have a basis weight of about 150 grams per square meter or less, and a fluid centrifuge retention capacity of about 10 grams 0.9 weight percent saline per gram substrate or less. Advantageously, the substrate 12 may be a sheet having a peak tensile strength under load of at least about 50 grams per centimeter width. Suitable substrates 12 include, but are not limited to, nonwoven, woven, and knitted fabrics; cellulosic tissue sheets; plastic films, including polypropylene, low density polyethylene, high density polyethylene, linear low density polyethylene, and ultra low density polyethylene; styrene-ethylene-butylene-styrene or styrene-isoprene-styrene block copolymers, KRATON polymers from Kraton Polymers of Houston, Tex., metallocene catalyzed elastomers or plastomers, and the like or combinations thereof. Other suitable substrates include monolithic breathable films, such as those made of polyether amide based polymers, for example PEBAX available from Autofina Chemical Company of Philadelphia, Pa., and ether/ester polyurethane thermal-plastic elastomers; LYCRA stranded composites; and elastomer net composites.

In another aspect, the substrate 12 may be a multi-functional substrate having an average basis weight of about 150 grams per square meter or less and a fluid centrifuge retention capacity of about 10 grams 0.9 weight percent saline per gram multi-functional substrate or less. Advantageously, the multi-functional substrate 12 may be a sheet having a peak tensile strength under load of at least about 50 grams per centimeter width. Suitably, the multi-functional substrate includes a plurality of regions. Each region may have similar physical characteristics or the regions may have different physical characteristics. For example, a multi-functional substrate may include at least two regions having different densities and/or may include at least one apertured region and at least one unapertured region.

Optionally, the substrate 12 may be treated with a fluid modifying material such as, for example, a viscoelastant or a surfactant. A "viscoelastant" is an organic agent that, when an effective amount is contacted by a viscoelastic composition, materially alters the properties of that viscoelastic composition, for example, by reducing its viscosity and/or elastic nature. A viscoelastant may be applied to at least a portion of the substrate 12 as a menses modifying material and/or a feces-modifying material.

A suitable viscoelastant for use in the present invention includes an alkyl polyglycoside including 8-10 carbon atoms in the alkyl chain. Alkyl polyglycosides alter the viscoelastic properties of viscoelastic fluids such as menses and feces as well as increase the wettability of synthetic surfaces. One specific viscoelastant suitable for use in the present invention is an alkyl polyglycoside available under the trademark GLUCOPON 220UP from Cognis Corporation of Ambler, Pa.

Other examples of suitable viscoelastants include bovine lipid extract surfactant, available under the registered trademark SURVANTA from Ross Laboratories of Columbus, Ohio, a drug used to treat Acute Respiratory Distress Syndrome and Cystic Fibrosis, and enzymes such as papain and pepsin which cleave protein structures. Some dextrins and dextrans may also be used a viscoelastants. Dextrans (macrose) are polymers of glucose with chain-like structures and molecular weight of, for example, about 200,000 or less produced from sucrose, often by bacterial action. Dextrins (starch gum) are normally solid starch derivatives formed when starch is heated either alone or with nitric acid. A suitable dextran for use in the present invention includes a 4000 MW oligosaccharide available from Polydex Pharmaceuticals, Ltd. of Scarborough, Ontario, Canada.

The addition of the viscoelastant to the substrate may be accomplished by conventional means such as spraying, coating, dipping and the like. Alternatively, in some cases it may be advantageous to add the viscoelastant as an internal additive to the polymer melt used to form the substrate. The amount of viscoelastant applied will depend upon the particular end use as well as factors such as basis weight and porosity of the substrate. Other examples of viscoelastants and methods of application are disclosed in commonly assigned U.S. Pat. No. 6,060,636 to Yahiaoui et al., which is incorporated by reference.

Surfactants may be applied to the substrate 12 in order to improve the fluid permeability or wettability of the substrate, particularly those including substantially hydrophobic materials such as polypropylene, polyethylene, and the like. Suitable surfactants may include amphoteric, anionic, cationic, nonionic, and zwitterionic surfactants. For example, the substrate 12 may be treated with about 0.45 weight percent of a surfactant mixture including AHCOVEL N-62 available from Uniqema Inc., a division of ICI of New Castle, Del., U.S.A. and GLUCOPON 220UP available from Cognis Corporation of Ambler, Pa., and produced in Cincinnati, Ohio, in an active ratio of 3:1. The surfactant can be applied by any conventional means, such as spraying, printing, brush coating or the like. The surfactant can be applied to the entire substrate 12 or can be selectively applied to particular regions or surfaces of the substrate 12, such as a medial region along a longitudinal centerline or either a top surface or an opposing bottom surface.

Figure 2A:
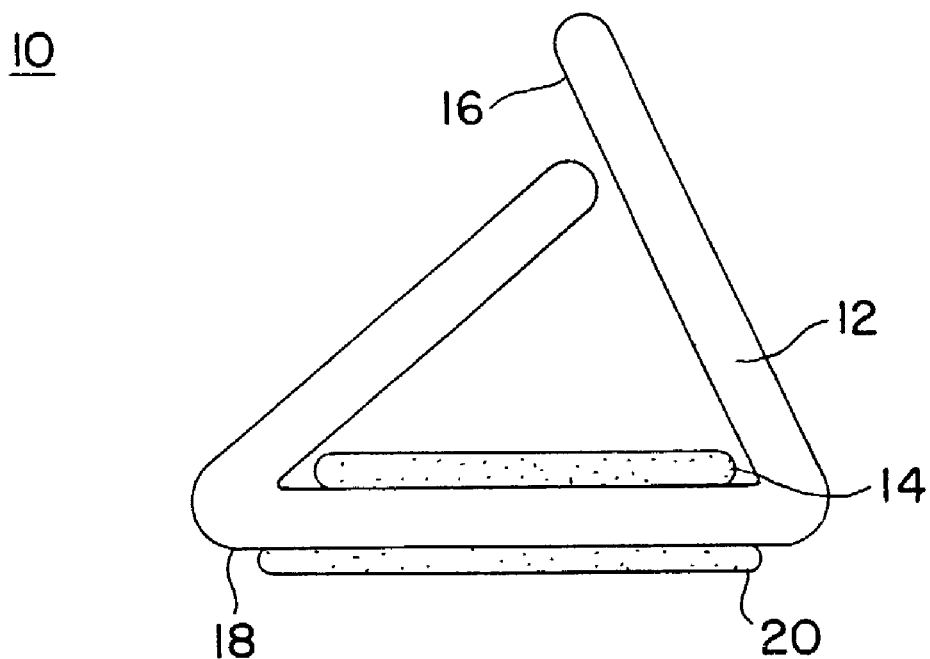
FIGS. 2a and 2b illustrate representative absorbent composites of the present invention including a layer of an adhesive material.
Figure 2B:
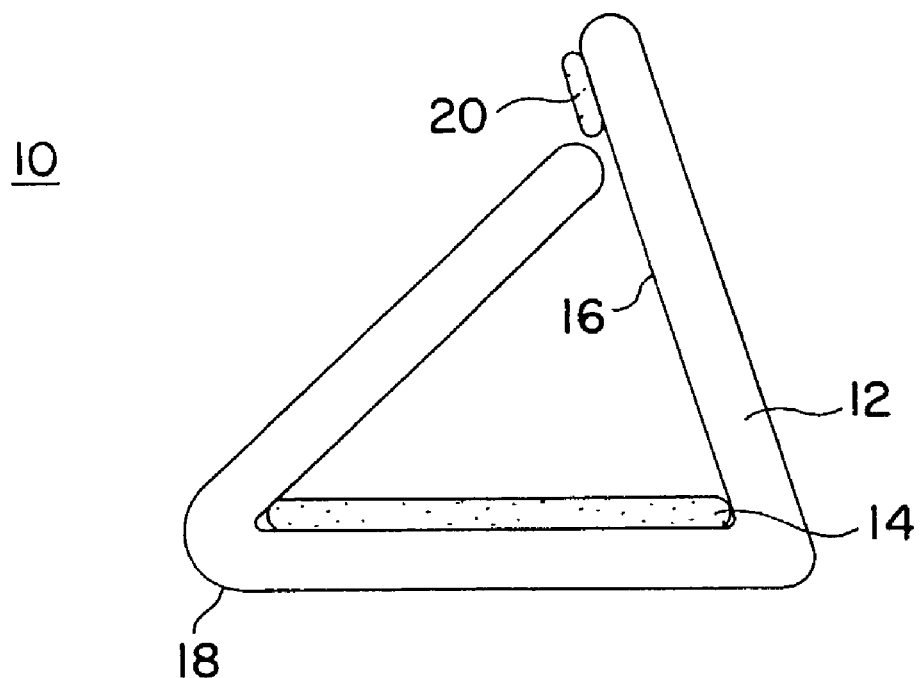

Additionally, the substrate 12 may be coated with a moisture-insensitive adhesive material. The moisture-insensitive adhesive material may be used to form a fluid barrier on one or more surfaces of the substrate or may be used to secure the substrate in a folded configuration. For example, referring to FIG. 2a, at least a portion of a bottom surface 18 of the substrate 12 may be coated with a layer of a moisture-insensitive adhesive material 20 to form a fluid barrier. Alternatively, as shown in FIG. 2b, at least a portion of a top surface 16 of the substrate 12 may be coated with a layer of a moisture-insensitive adhesive material 20 to secure the substrate 12 in a folded configuration. The moisture-insensitive adhesive material may also be coated onto the substrate in other configurations to assist in distributing fluid within the absorbent composite or may be overlaid with the absorbent adhesive composition. Suitable moisture-insensitive adhesive materials, which can be applied continuously or intermittently as beads, a spray, parallel swirls, or the like, can be obtained from Findley Adhesives, Inc., of Wauwatosa, Wis., or from National Starch and Chemical Company, Bridgewater, N.J.

The absorbent composite 10 includes an absorbent adhesive composition coated onto at least a portion of the substrate 12. The absorbent adhesive composition may be an absorbent binder or an absorbent in situ neutralizable binder composition used alone or in combination with a superabsorbent material, a fluid modifying material and/or an odor control agent. For example, the absorbent adhesive composition may be an absorbent binder, an absorbent binder/superabsorbent combination, an absorbent in situ neutralizable binder composition, or an absorbent in situ neutralizable binder composition/superabsorbent material combination.

One suitable absorbent binder includes an absorbent crosslinkable binder composition. The absorbent crosslinkable binder composition may include soluble polymers such as hydrophilic polymers, or blends of hydrophilic polymers or hydrophobic polymers containing hydrophilic agents. Suitably, the crosslinkable binder composition may include a latent crosslinker composed of multivalent metal ions. An example of a suitable binder includes an alkoxysilane grafted poly(ethylene oxide) ("gPEO") that is soluble in alcohol solvents that do not substantially swell or dissolve superabsorbent material. As used herein, the term "substantially swell" refers to a substance that causes a particle to swell, thereby increasing in volume by at least 10 percent. More specifically, the gPEO, upon exposure to moisture, crosslinks into a gel structure capable of absorbing relatively large amounts of fluids, such as water or saline. This type of binder is capable of crosslinking during the solvent drying or evaporating process to provide enhanced wet attachment. Methacryloxypropyl trimethoxy silane is one example of a suitable alkoxysilane grafting monomer.

Poly(ethylene oxide) ("PEO") is one of a very few polymers that is both water-soluble and thermally processable. PEO has also been shown to be biodegradable under a variety of conditions. Initial work has been done with PEO N-80 (molecular weight about 200,000) which is commercially available from Union Carbide of Danbury, Conn. This grade of PEO is suitable for extrusion processing into film.

In accordance with the present invention, PEO is graft polymerized with an organic moiety capable of graft polymerization with PEO which moiety contains a trialkoxy silane functional group or which moiety reacts with water to form a silanol group. The silane graft modified PEO resin can be thermally processed into functional forms, such as films, fibers and foams. When these functional forms are exposed to moisture, a crosslinking reaction occurs to provide a gel structure capable of absorbing relatively large amounts of water, such as 20 grams of saline per gram of polymer or more under free swell conditions, making such materials ideal for an absorbent structure.

Water-soluble polymers useful in the present invention include, but are not limited to, poly(alkylene oxides), such as poly(ethylene oxide) ("PEO"), poly(ethylene glycols), block copolymers of ethylene oxide and propylene oxide, poly(vinyl alcohol) and poly(alkyl vinyl ethers). These water-soluble polymers must be capable of graft polymerization with an organic moiety containing a trialkoxy silane functional group or a moiety that reacts with water to form a silanol group. The preferred water-soluble polymer for use in the present invention is PEO.

The PEO resins useful for graft modification in accordance with the present invention include, but are not limited to, PEO resins having initial reported approximate molecular weights ranging from about 30,000 g/mol to about 8,000,000 g/mol as determined by Theological measurements. All molecular weights are given on a weight average basis unless otherwise indicated.

Such PEO resins are commercially available from, for example, Union Carbide Corporation having offices in Danbury, Conn., and are sold under the trade designations POLYOX 205, POLYOX N-10, POLYOX N-80, POLYOX WSR N-750, POLYOX WSR N-12K and POLYOX UCAR-FLOC Polymer 309.

The PEO resins and modified compositions may optionally contain various additives, such as plasticizers, processing aids, rheology modifiers, antioxidants, UV light stabilizers, pigments, colorants, slip additives, antiblock agents, etc., which may be added before or after modification.

Organic monomers capable of graft polymerization with PEO, which monomers contain a trialkoxy silane functional group or a moiety that reacts with water to form a silanol group, are useful in the practice of this invention. The term "monomer(s)" as used herein includes monomers, oligomers, polymers, mixtures of monomers, oligomers and/or polymers, and any other reactive chemical species which is capable of covalent bonding with the parent polymer, PEO. Ethylenically unsaturated monomers containing a trialkoxy silane functional group are appropriate for this invention and are desired. Desired ethylenically unsaturated monomers include acrylates and methacrylates. A particularly desirable ethylenically unsaturated monomer containing a trialkoxy silane functional group is methacryloxypropyl trimethoxy silane, which is commercially available from Dow Corning, having offices in Midland, Mich., under the trade designation Z-6030 Silane. Other suitable ethylenically unsaturated monomers containing a trialkoxy silane functional group include, but are not limited to, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy) silane. However, it is contemplated that a wide range of vinyl and acrylic monomers having trialkoxy silane functional groups or a moiety that reacts easily with water to form a silanol group, such as a chlorosilane or an acetoxysilane, provide the desired effects to PEO and are effective monomers for grafting in accordance with the present invention.

The amount of organic monomer having trialkoxy silane functional groups or silanol-forming functional groups relative to the amount of PEO may range from about 0.1 to about 20 weight percent of monomer to the weight of PEO. Desirably, the amount of monomer should exceed 0.1 weight percent in order to sufficiently improve the processability of the PEO. Typically, the monomer addition levels are between about 1.0 percent and about 15 percent of the weight of the base PEO resin; particularly, between about 1.0 percent and about 10 percent of the weight of the base PEO resin; especially, between about 1.5 percent and about 5.5 percent of the weight of the base PEO resin for some intended uses. Suitably, the grafting level may be in the range of 0.5 to about 10 weight percent relative to the weight of the PEO.

The binders used in the invention should provide very flexible coatings and should therefore have a glass transition temperature about 30 degrees Celsius or lower, or about 10 degrees Celsius or lower, as measured by a Differential Scanning Calorimeter (DSC). The crosslinkable binder composition desirably has a bending modulus lower than the bending modulus of the substrate.

When grafting is achieved by the application of heat, as in a reactive-extrusion process, it is desirable that the initiator generates free radicals through the application of heat. Such initiators are generally referred to as thermal initiators. For the initiator to function as a useful source of radicals for grafting, the initiator should be commercially and readily available, stable at ambient or refrigerated conditions, and generate radicals at reactive-extrusion temperatures.

Compounds containing an O—O, S—S, or N=N bond may be used as thermal initiators. Compounds containing O—O bonds; i.e., peroxides, are commonly used as initiators for graft polymerization. Such commonly used peroxide initiators include: alkyl, dialkyl, diaryl and arylalkyl peroxides such as cumyl peroxide, t-butyl peroxide, di-t-butyl peroxide, dicumyl peroxide, cumyl butyl peroxide, 1,1-di-t-butyl peroxy-3,5,5-trimethylcyclohexane, 2,5-dimethyl-2,5-di(t-butylperoxy)hexane, 2,5-dimethyl-2,5-bis(t-butylperoxy)hexyne-3 and bis(a-t-butyl peroxyisopropylbenzene); acyl peroxides such as acetyl peroxides and benzoyl peroxides; hydroperoxides such as cumyl hydroperoxide, t-butyl hydroperoxide, p-methane hydroperoxide, pinane hydroperoxide and cumene hydroperoxide; peresters or peroxyesters such as t-butyl peroxypivalate, t-butyl peroctoate, t-butyl perbenzoate, 2,5-dimethylhexyl-2,5-di(perbenzoate) and t-butyl di(perphthalate); alkylsulfonyl peroxides; dialkyl peroxymonocarbonates; dialkyl peroxydicarbonates; diperoxyketals; ketone peroxides such as cyclohexanone peroxide and methyl ethyl ketone peroxide. Additionally, azo compounds such as 2,2'-azobisisobutyronitrile abbreviated as AIBN, 2,2'-azobis(2,4-dimethylpentanenitrile) and 1,1'-azobis(cyclohexanecarbonitrile) may be used as the initiator. Examples of commercially available initiators include a liquid, organic peroxide initiator available from R.T. Vanderbilt Company, Inc. of Norwalk, Conn., sold under the trade designation VAROX DBPH peroxide which is a free radical initiator and comprises 2,5-bis(tert butylperoxy)-2,5-dimethyl hexane along with smaller amounts of di(tert butylperoxide). Other initiators include LUPERSOL 101 and LUPERSOL 130 available from Elf Atochem North America, Inc. of Philadelphia, Pa.

Other suitable binders comprise monoethylenically unsaturated carboxylic, sulphonic or phosphoric acids, or salts thereof, and an acrylate or methacrylate ester that contains an alkoxysilane functionality which, upon exposure to water, forms a silanol functional group which condenses to form a crosslinked polymer.

Desired monomers include carboxyl group-containing monomers: monoethylenically unsaturated mono or polycarboxylic acids, such as (meth)acrylic acid (meaning acrylic acid or methacrylic acid—similar notations are used hereinafter to denote various copolymers), maleic acid, fumaric acid, crotonic acid, sorbic acid, itaconic acid, and cinnamic acid;

Carboxylic acid anhydride group-containing monomers: monoethylenically unsaturated polycarboxylic acid anhydrides (such as maleic anhydride);

Carboxylic acid salt-containing monomers: water-soluble salts (alkali metal salts, ammonium salts, amine salts, etc.) of monoethylenically unsaturated mono- or poly-carboxylic acids (such as sodium (meth)acrylate, trimethylamine (meth)acrylate, triethanolamine (meth)acrylate, sodium maleate, methylamine maleate;

Sulfonic acid group-containing monomers: aliphatic or aromatic vinyl sulfonic acids (such as vinylsulfonic acid, allyl sulfonic acid, vinyltoluenesulfonic acid, stryrene sulfonic acid), (meth)acrylic sulfonic acids [such as sulfopropyl (meth)acrylate, 2-hydroxy-3-(meth)acryloxy propyl sulfonic acid];

Sulfonic acid salt group-containing monomers: alkali metal salts, ammonium salts, amine salts of sulfonic acid group containing monomers as mentioned above; and Amide group-containing monomers: vinylformamide, (meth)acrylamide, N-alkyl (meth)acrylamides (such as N-methylacrylamide, N-hexylacrylamide), N,N-dialkyl (meth)acrylamides (such as N,N-dimethylacrylamide, N,N-di-n-propylacrylamide), N-hydroxyalkyl (meth)acrylamides (such as N-methylol (meth)acrylamide, N-hydroxyethyl (meth)acrylamide), N,N-dihydroxyalkyl (meth)acrylamides (such as N,N-dihydroxyethyl (meth)acrylamide), vinyl lactams (such as N-vinylpyrrolidone).

The amount of monoethylenically unsaturated carboxylic, sulphonic or phosphoric acid or salts thereof relative to the weight of the polymeric binder composition may range from about 20 to about 99.9 weight percent. Typically, the monoethylenically unsaturated carboxylic, sulphonic or phosphoric acid or salts thereof levels are between about 25 percent and about 90 percent of the weight of the polymeric binder composition; particularly, between about 30 percent and about 80 percent of the weight of the polymeric binder composition; especially, between about 50 percent and about 70 percent of the weight of the polymeric binder composition for some intended uses.

Organic monomers capable of co-polymerization with monoethylenically unsaturated carboxylic, sulphonic or phosphoric acid or salts thereof, which monomers contain a trialkoxy silane functional group or a moiety that reacts with water to form a silanol group, are useful in the practice of this invention. The term "monomer(s)" as used herein includes monomers, oligomers, polymers, mixtures of monomers, oligomers and/or polymers, and any other reactive chemical species which is capable of co-polymerization with monoethylenically unsaturated carboxylic, sulphonic or phosphoric acid or salts thereof. Ethylenically unsaturated monomers containing a trialkoxy silane functional group are appropriate for this invention and are desired. Desired ethylenically unsaturated monomers include acrylates and methacrylates. A particularly desirable ethylenically unsaturated monomer containing a trialkoxy silane functional group is methacryloxypropyl trimethoxy silane, commercially available from Dow Corning, having offices in Midland, Mich., under the trade designation Z-6030 Silane. Other suitable ethylenically unsaturated monomers containing a trialkoxy silane functional group include, but are not limited to, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy) silane. However, it is contemplated that a wide range of vinyl and acrylic monomers having trialkoxy silane functional groups or a moiety that reacts easily with water to form a silanol group, such as a chlorosilane or an acetoxysilane, are effective monomers for copolymerization in accordance with the present invention.

In addition to monomers capable of co-polymerization that contain a trialkoxy silane functional group, it is also feasible to use a monomer capable of co-polymerization that can subsequently be reacted with a compound containing a trialkoxy silane functional group or a moiety that reacts with water to form a silanol group. Such a monomer may contain, but is not limited to, an amine or an alcohol. An amine group incorporated into the co-polymer may subsequently be reacted with, for example but not limited to, (3-chloropropyl)trimethoxysilane. An alcohol group incorporated into the co-polymer may subsequently be reacted with, for example but not limited to, trimethoxysilane.

The amount of organic monomer having trialkoxy silane functional groups or silanol-forming functional groups relative to the weight of the polymeric binder composition may range from about 0.1 to about 15 weight percent. Desirably, the amount of monomer should exceed 0.1 weight percent in order to provide sufficient crosslinking upon exposure to moisture. Typically, the monomer addition levels are between about 1.0 percent and about 15 percent of the weight of the polymeric binder composition; particularly, between about 1.0 percent and about 10 percent of the weight of the polymeric binder composition; especially, between about 1.5 percent and about 5.5 percent of the weight of the polymeric binder composition for some intended uses.

Optionally, the polymeric binder may include long chain, hydrophilic monoethylenically unsaturated esters, such as poly(ethylene glycol) methacrylate having from 1 to 13 ethylene glycol units, particularly, between 2 and 10 ethylene glycol units; especially, between 3 and 6 ethylene glycol units.

Suitable acrylic acid salts for use in combination with poly(ethylene glycol) methacrylate include sodium acrylate, potassium acrylate, ammonium acrylate, and quaternary amine acrylate.

The amount of monoethylenically unsaturated hydrophilic esters relative to the weight of the polymeric binder composition thereof may range from about 0 to about 75 weight percent of monomer to the weight of the polymeric binder composition. Typically, the monomer addition levels are between about 10 percent and about 60 percent of the weight of the polymeric binder composition; particularly, between about 20 percent and about 50 percent of the weight of the polymeric binder composition; especially, between about 30 percent and about 40 percent of the weight of the polymeric binder composition for some intended uses.

In addition, polymer modifying agents such as compatible polymers, plasticizers, colorants, stabilizers, flow aids, and preservatives may be incorporated in the binder composition.

Another suitable absorbent adhesive composition may include an absorbent in situ neutralizable binder composition. The absorbent in situ neutralizable binder composition may include a copolymer of an unneutralized polyacid and a polyamine binder material. The unneutralized polyacid may be selected from poly(acrylic acid), poly(methacrylic acid), poly(maleic acid), carboxymethyl cellulose, alginic acid, poly(aspartic acid), and poly(glutamic acid). Suitably, the polyacid includes poly(acrylic acid). The polyamine binder material may be selected from poly(vinylamine), a polyethylenimine, a poly(vinylguanidine), a poly(allylamine), a poly(allylguanidine), and a poly(dialkylaminoalkyl (meth)acrylamide). Suitably, the polyamine binder material includes poly(vinylamine).

Figure 3A:
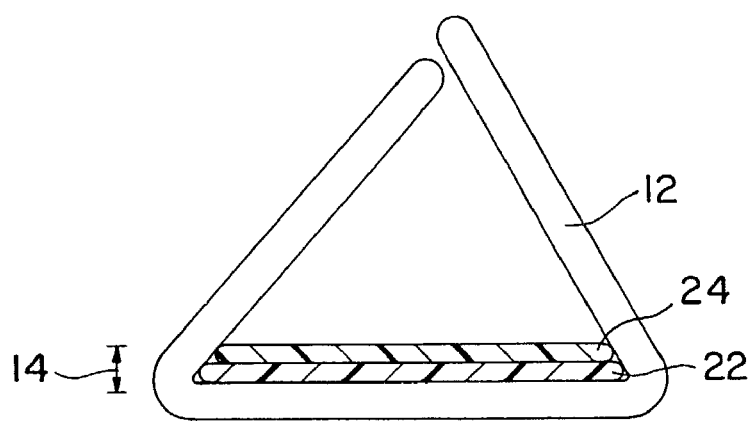
FIGS. 3a through 3c illustrate representative absorbent composites of the present invention including an absorbent in situ neutralizable binder composition.
Figure 3B:
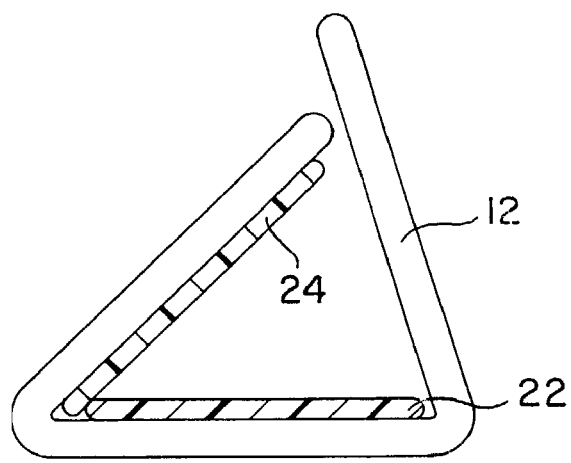
Figure 3C:
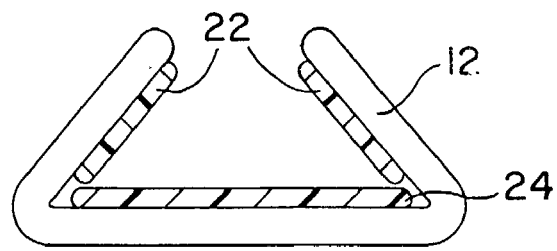

Desirably, the copolymer of an unneutralized polyacid and the polyamine binder material are coated onto the substrate 12 as one or more separate layers. For example, referring to FIGS. 3a through 3c, one or more layers of a copolymer of an unneutralized polyacid 22 are coated onto the substrate 12 and one or more layers of the polyamine binder material 24 are coated onto the same or different portions of the substrate such that when the substrate 12 is folded layer or layers 22 and 24 are brought together. Without wishing to be bound by theory, it is believed that providing a copolymer of an unneutralized polyacid together with a polyamine binder material forms a macro bipolar absorbent film that is capable of desalinating an electrolyte-containing fluid. Desalinating the electrolyte-containing solution is believed to aid in fluid absorption and retention within the absorbent composite 10, especially when the absorbent adhesive composition includes a superabsorbent material, by inhibiting or preventing a salt poisoning effect which may reduce the capacity of the absorbent adhesive composition and/or the superabsorbent material. The layers 22 and 24 may be applied to the substrate 12 in any configuration that brings layer 22 together with layer 24. For example, the layer 22 may be brought into direct contact with layer 24. Alternatively, a third layer, such as a nonionic, liquid permeable membrane or an open structure such as a screen can be used as a mediator to allow the reaction between layer 22 and layer 24 to occur.

In one embodiment, the absorbent adhesive composition may include a superabsorbent material. The superabsorbent material may be of any suitable chemistry to provide absorbency under anticipated usage conditions. Suitable chemistries include crosslinked forms of sodium polyacrylate, sodium polymethacrylate, polyacrylamide, carboxymethyl cellulose, grafted starch, poly(sodium aspartate), poly(vinyl amine), poly(dimethyldiallyl amine), chitosan salt, and/or poly(ethylene imine). Superabsorbent materials are available from various commercial vendors, such as Dow Chemical Company located in Midland, Mich., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water. The superabsorbent material may be present in the absorbent composite 10 in an amount of up to about 95 weight percent based on the total weight of the absorbent adhesive composition and the superabsorbent material.

Particle size and geometry of the superabsorbent material may be whatever is suitable for a particular means of applying the superabsorbent material in solution to the substrate 12. For example, the superabsorbent material may be spherical, platelet-like, fibrous, or any related geometry. In the unswollen state, the superabsorbent material may have cross-sectional diameters in a range from about 50 to about 800 microns, or from about 200 to about 400 microns, and for some printing applications from about 60 to about 80 microns, as determined by sieve analysis according to the American Society for Testing Materials (ASTM) Test Method D-1921. It is understood that the particles of material falling within these ranges may include solid particles, porous particles, or may be agglomerated particles including many smaller particles agglomerated into particles within the described size ranges.

Advantageously, the absorbent adhesive composition may be dissolved or dispersed in a solvent. Suitable solvents include any solvents that provide for solubility of the absorbent binder or absorbent in situ neutralizable binder composition without swelling the superabsorbent material, such that the dry weight of the superabsorbent material is increased by no more than 10 percent as a result of imbibing solvent. Alternatively, no more than 1 percent by weight gain resulting from solvent is imbibed by the superabsorbent material. The amount of solvent may be chosen to provide the appropriate flow properties for the absorbent adhesive composition that is appropriate for the chosen application process. As mentioned, alcohol solvents may be used in the absorbent binder. In one embodiment, the alcohol solvent may include between about 99.5 percent and about 50 percent alcohol by weight, and between about 0.5 percent and about 50 percent water by weight. Ethanol is one example of a suitable alcohol solvent.

A process for making an absorbent composite includes the steps of: providing a substrate; applying an absorbent adhesive composition to at least a portion of the substrate; and folding the substrate upon itself to provide a plurality of panels. The absorbent adhesive composition may be applied as a solution or dispersion in a solvent. If superabsorbent material is included in the absorbent adhesive composition, the superabsorbent particles and/or fibers may be dispersed in a solvent with an absorbent adhesive composition.

The absorbent adhesive composition may be applied to the substrate using any suitable application process, including knife over roll coating, or roll coating, either in a continuous coverage or a patterned coverage. Printing applications are other suitable application techniques, including gravure printing, screen, and jet printing. The absorbent adhesive composition may also be applied to the substrate using a spray application. Alternatively, the absorbent adhesive composition may be heated to a flowable condition and extruded onto the substrate. Superabsorbent material may be added to the absorbent adhesive composition either prior to extrusion coating the flowable absorbent adhesive composition or subsequent to extrusion coating the flowable absorbent adhesive composition onto the substrate. If applied after extrusion, the superabsorbent particles and/or fibers may be pressed into the absorbent adhesive composition once the absorbent adhesive composition is on the substrate.

Desirably, the absorbent adhesive composition is applied to or coated onto at least a portion of the substrate 12. Advantageously, at least a portion of the substrate remains uncoated. The absorbent adhesive composition may be applied to or coated onto the substrate in any suitable manner. For example, referring to FIGS. 4a through 4d, the absorbent adhesive composition may be applied as a continuous layer, in an offset pattern, or in a gradient pattern. Alternatively, the absorbent adhesive composition may be applied in a discontinuous dot pattern.

Figure 4A:
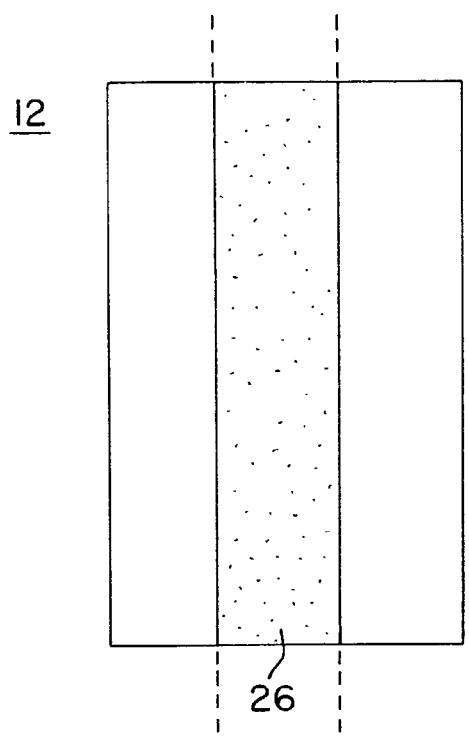
FIGS. 4a through 4d illustrate representative patterns of application of an absorbent adhesive composition.
Figure 4B:
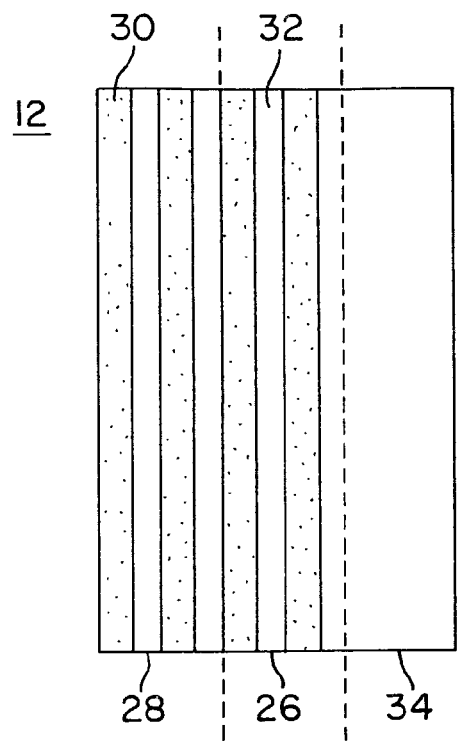

Referring to FIG. 4a, one suitable application pattern includes coating a central region 26 with the absorbent adhesive composition. Another suitable application pattern, shown in FIG. 4b, includes coating a first region 28 of a substrate 12 with a discontinuous pattern of an absorbent adhesive composition and coating a central region 26 of the substrate 12 with an offset discontinuous pattern of the absorbent adhesive composition such that when the substrate 12 is folded the coated portions 30 of the first region 28 overlay the uncoated portions 32 of the central region 26. Desirably, a second region 34 of the substrate 12 remains uncoated. The application pattern shown in FIG. 4b includes offset bands or stripes of the absorbent adhesive composition. However, the first region 28 and the central region 26 may be coated with any complementary pattern that allows the coated portions of one region to overlay the uncoated portions of the other region upon folding of the substrate. Alternatively, the second region 34 of the substrate 12 may be coated with a discontinuous pattern complementary to the central region 26 and the first region 28 may be uncoated.

Figure 4C:
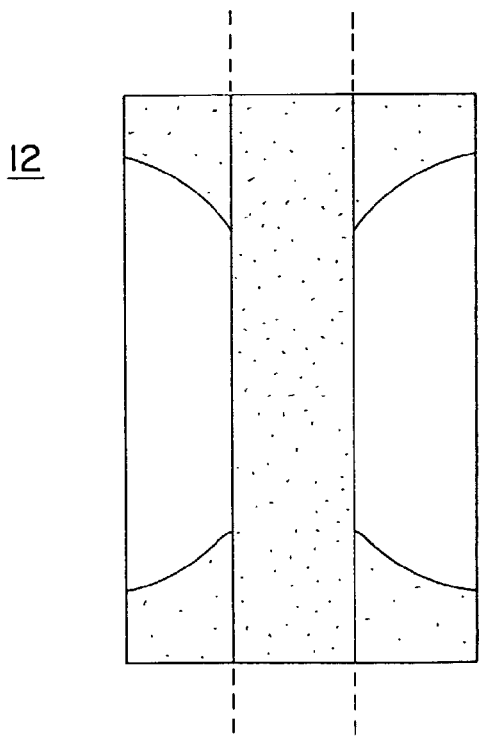
Figure 4D:
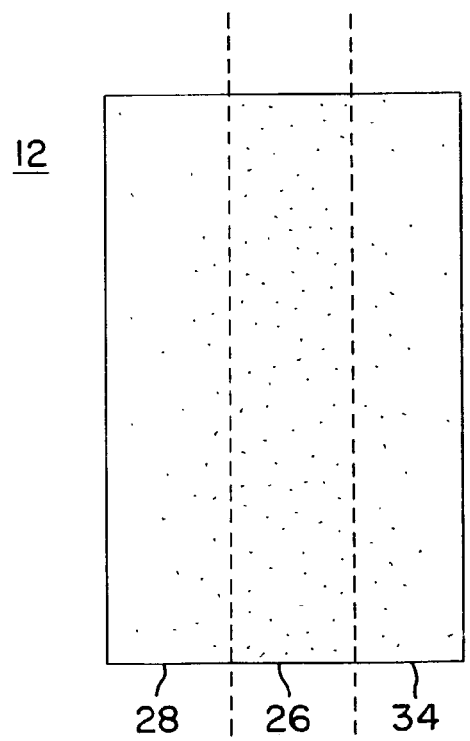

In an additional embodiment, as illustrated in FIG. 4c, the substrate 12 may be coated with the absorbent adhesive composition in the shape of an absorbent pad such as, for example, a diaper-shaped pad. The substrate may then be optionally cut and folded to provide an absorbent composite having a diaper or other shape. In a further embodiment, as depicted in FIG. 4d, the absorbent adhesive composition may be applied in a gradient pattern. For example, a substrate 12 may be coated with an amount of an absorbent adhesive composition that decreases from a central region 26 to adjacent first and second regions 28 and 34. Alternatively, a substrate 12 may be coated with an amount of an absorbent adhesive composition that increases from a central region 26 to adjacent first and second regions 28 and 24 (not shown).

If the absorbent adhesive composition is applied as a solution, the process for making the absorbent composite further includes the step of removing the solvent from the substrate. The solvent may be removed from the substrate either by drying the substrate or using any other effective technique to evaporate the solvent. If the absorbent adhesive composition is applied in a flowable condition, the process for making the absorbent composite further includes cooling the substrate to form a cohesive film or network. If superabsorbent material is included in the absorbent adhesive composition, the particles or fibers will be adhered to each other and/or the substrate by the adhesive composition or binder.

If the absorbent adhesive composition includes an absorbent crosslinkable binder composition, the process for making an absorbent composite further includes inducing crosslinking of the binder after the absorbent adhesive composition has been applied to the substrate. Crosslinking may be induced by a variety of techniques including thermal initiation, radiation initiation, redox chemical reactions, multivalent metal ions, and moisture. Various types of effective radiation initiation include ultraviolet, microwave, and electron-beam radiation. Moisture initiation may be accomplished through hydrolysis and condensation. Multivalent metal ions can initiate crosslinking by complexation. After inducing crosslinking of the binder, the solvent (if present) can be removed from the substrate, either by drying the substrate or using any other effective technique to evaporate the solvent.

After the absorbent adhesive composition is applied to at least a portion of the substrate 12, the substrate is folded to provide a plurality of panels. The coated substrate 12 may be folded in any manner in order to provide an absorbent composite 10 having at least two panels. Desirably, the coated substrate 12 is folded such that the absorbent adhesive composition is enclosed or enveloped by the substrate 12. Folding in this manner is desirable in order to inhibit and/or prevent the absorbent adhesive composition from expanding significantly in the x-y plane. This aids in preventing leakage of fluid and/or the absorbent adhesive composition from the absorbent composite. Suitably, the substrate 12 is folded such that at least a portion of the uncoated substrate is situated to provide at least one of the desired fluid handling functions.

Figure 5:
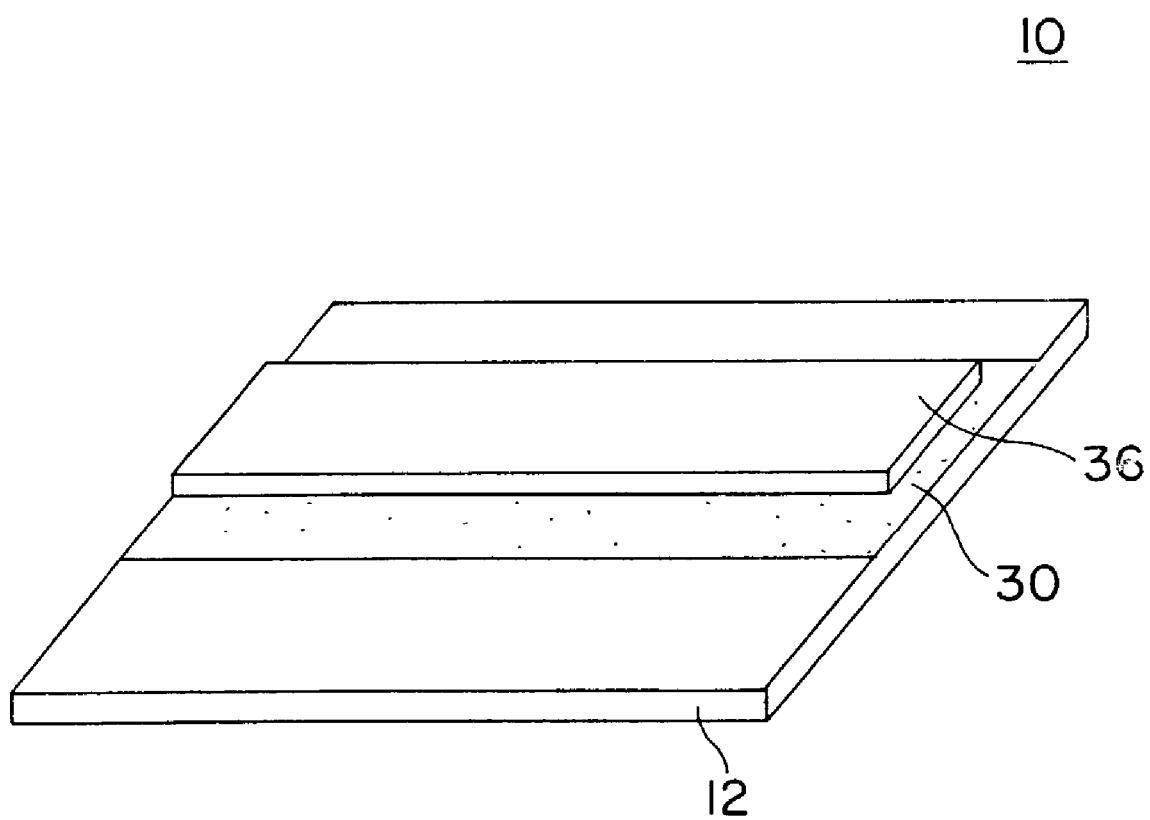
FIG. 5 illustrates a representative absorbent composite of the present invention including an additional sheet or layer of material.

Optionally, prior to folding, an additional layer of material may be positioned adjacent a coated portion of a substrate 12 to provide one or more additional fluid handling functions. Desirably, any additional layers of material should be relatively thin so as to avoid adding significant bulk to the absorbent composite. Suitable additional materials that may be added to the absorbent composite include, but are not limited to, surge layers, wicking layers, film layers, and/or additional binder materials. For example, as illustrated in FIG. 5, an additional sheet of material 36 may be positioned adjacent a coated portion 30 of a substrate 12 such that when the substrate 12 is folded the sheet 36 is enclosed or enveloped within the absorbent composite 10. As shown in FIG. 5, the sheet 36 is positioned such that it overlays the coated portion 30 of the substrate 12. However, the sheet 36 may be positioned adjacent any portion of the substrate 12 such that when the substrate is folded the sheet 36 is positioned adjacent the coated portion 30 of the substrate and is enclosed within the absorbent composite 10. Suitably, the sheet 36 may provide the same fluid handling function as the substrate 12. Alternatively, the sheet 36 may provide a different fluid handling function than the substrate 12. The sheet 36 may be of any dimension such that it is enclosed within the absorbent composite 10 when the substrate 12 is folded. In a specific example of the embodiment depicted in FIG. 5, the substrate 12 may be a nonwoven material with an open structure. The sheet 36 may be a cellulosic material such as, for example, an uncreped-through-air-dried tissue. The resulting absorbent composite 10 may thus exhibit at least three fluid handling functionalities: retention provided by the absorbent adhesive composition; intake functionality provided by the nonwoven material; and distribution provided by the cellulosic material.

Figure 6A:
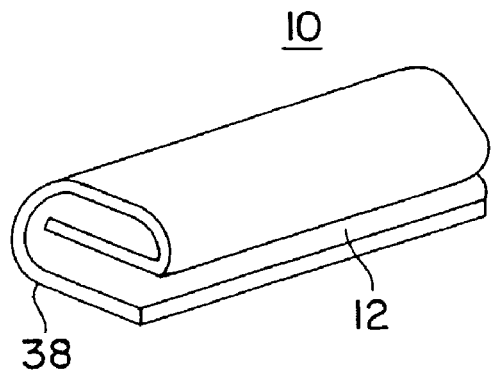
FIGS. 6a through 6d illustrate various folding stages of an absorbent composite having an "e"-shaped cross-section.
Figure 6B:
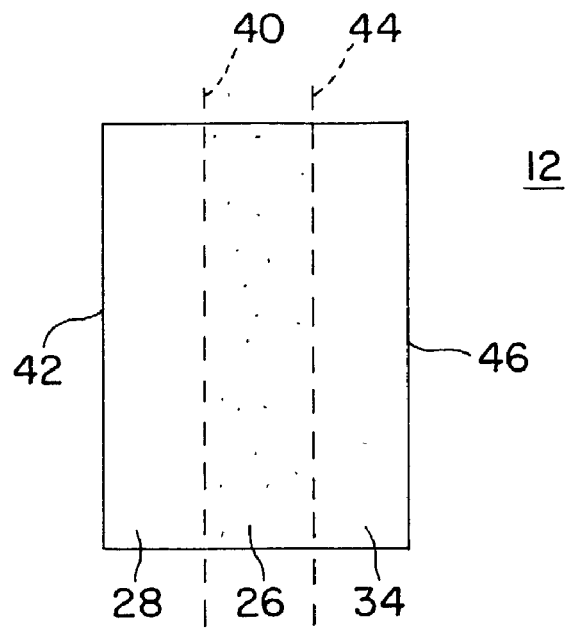
Figure 6C:
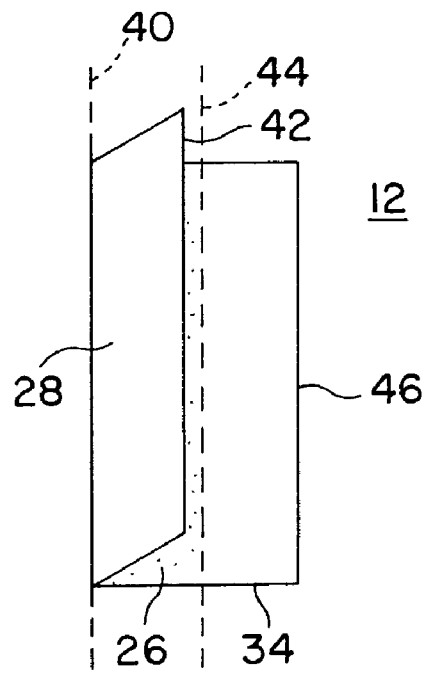
Figure 6D:
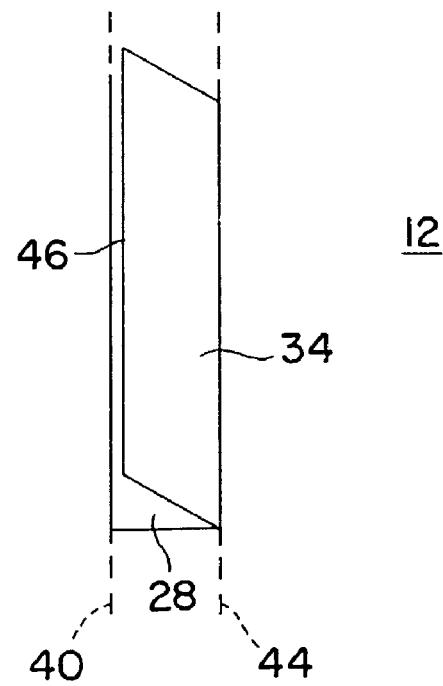

The substrate 12 may be folded to provide a specific cross-sectional profile. For example, as shown in FIG. 6a, the absorbent composite may have an "e"-shaped cross-section 38 formed by folding the substrate 12 in the manner illustrated in FIGS. 6b through 6d. Referring to FIG. 6b, a substrate 12 including a first region 28, a second region 34 and a central region 26 therebetween is coated with absorbent adhesive composition such that at least a portion of the first region 28 and/or the central region 26 is coated. Desirably, the second region 34 remains uncoated. The substrate 12 is folded along a first foldline 40 such that a first edge 42 of the substrate is positioned adjacent a second foldline 44 and the first region 28 overlays the central region 26 as shown in FIG. 6c. As shown in FIG. 6d, the substrate 12 is then folded along the second foldline 44 such that a second edge 46 of the substrate 12 is positioned adjacent the first foldline 40 and the second region 34 overlays the first region 28 to provide an absorbent composite 10 having an "e"-shaped cross-section 38. Alternatively, the substrate 12 could be folded in the reverse order such that the second region 34 overlays the central region 26 and the first region 28 overlays the second region 34 to provide an absorbent composite 10 having an "e"-shaped cross-section 38.

Figure 7A:
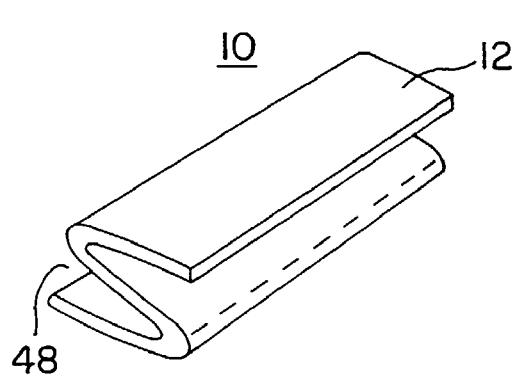
FIGS. 7a through 7d illustrate various folding stages of an absorbent composite having a "z"-shaped cross-section.
Figure 7B:
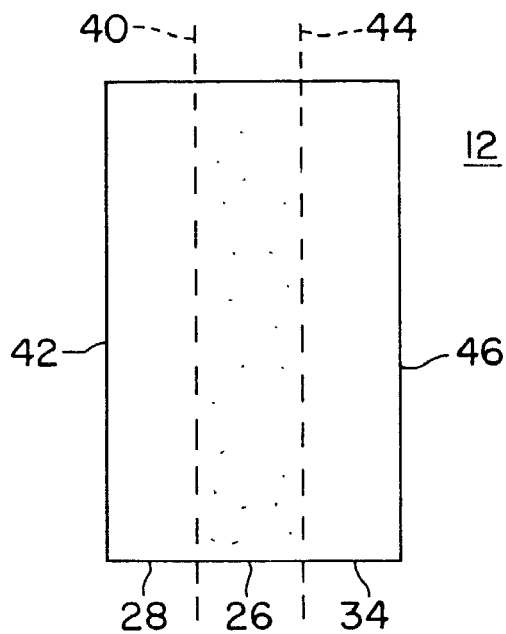
Figure 7C:
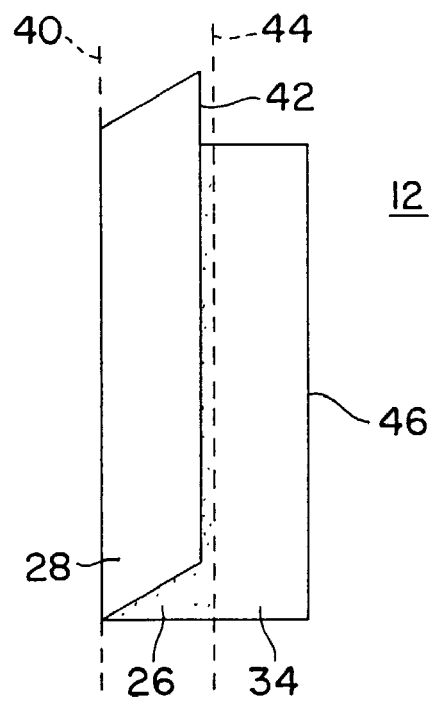
Figure 7D:
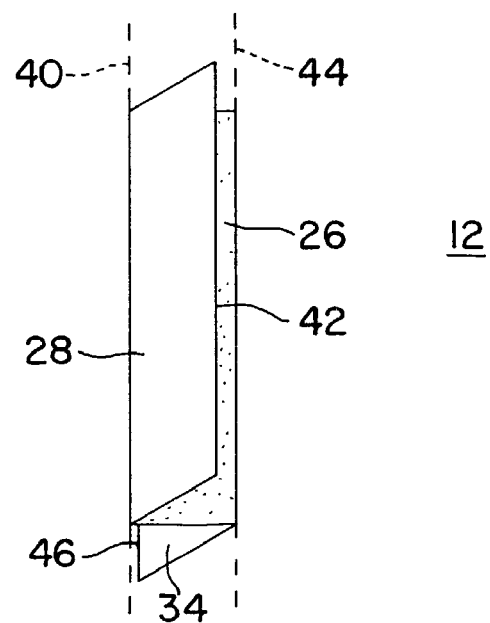

In another embodiment, the substrate 12 may be folded as shown in FIGS. 7b through 7d to provide a absorbent composite 10 having a "z"-shaped cross-section 48 as illustrated in FIG. 7a. Referring to FIG. 7b, a substrate 12 including a first region 28, a second region 34 and a central region 26 therebetween is coated with an absorbent adhesive composition such that at least a portion of the first region 28 and/or the central region 26 is coated. Desirably, the second region 34 remains uncoated. The substrate 12 is folded along a first foldline 40 such that a first edge 42 of the substrate is positioned adjacent a second foldline 44 and the first region 28 overlays the central region 26 as shown in FIG. 7c. As shown in FIG. 7d, the substrate 12 is then folded along the second foldline 44 such that a second edge 46 of the substrate is positioned adjacent the first foldline 40 and the second region 34 overlays the central region 26 on the opposite side to provide an absorbent composite 10 having a "z"-shaped cross-section 48. Alternatively, the substrate 12 could be folded in the reverse order such that the second region 34 overlays the central region 26 and the first region 28 overlays the central region 26 on the opposite side to provide an absorbent composite 10 having a "z"-shaped cross-section 48.

Figure 8A:
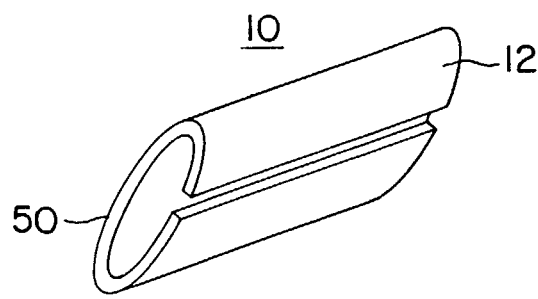
FIGS. 8a through 8d illustrate various folding stages of an absorbent composite having a "c"-shaped cross-section.
Figure 8B:
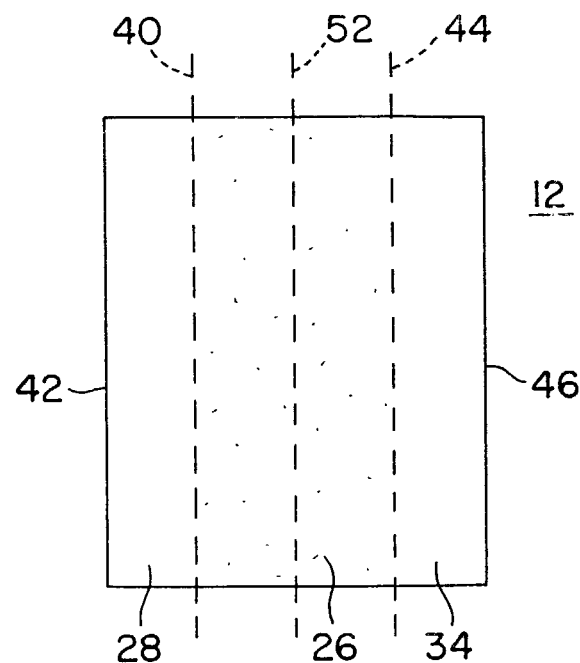
Figure 8C:
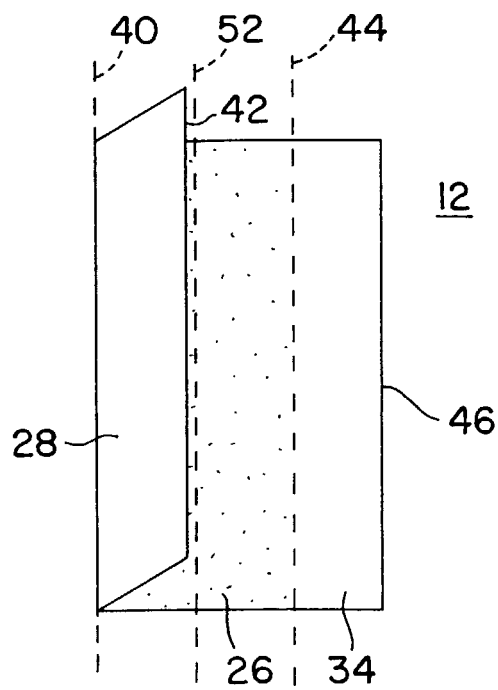
Figure 8D:
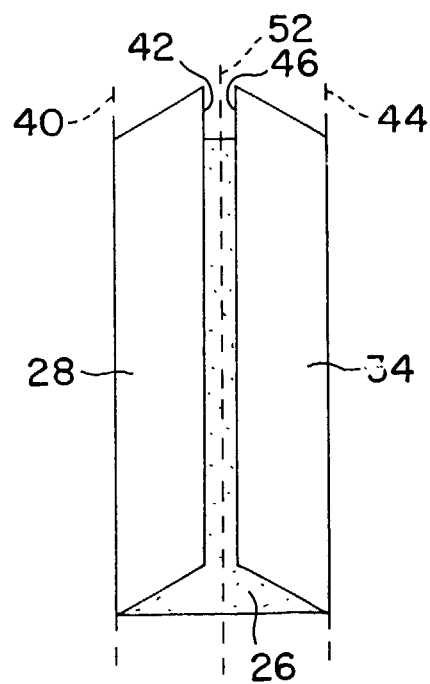

In a further embodiment, as illustrated in FIG. 8a, the absorbent composite 10 may have a "c"-shaped cross-section 50. Referring to FIG. 8b, a substrate 12 including a first region 28, a second region 34 and a central region 26 therebetween is coated with absorbent adhesive composition such that at least a portion of the central region 26 is coated. Desirably, the first region 28 and the second region 34 remain uncoated. Alternatively, at least a portion of the first region 28 and the second region 34 of the substrate 12 could be coated with absorbent adhesive composition while the central region 26 remains uncoated. The substrate 12 is folded along a first foldline 40 such that a first edge 42 of the substrate is positioned adjacent a longitudinal centerline 52 and the first region 28 overlays a portion of the central region 26 as shown in FIG. 8c. As shown in FIG. 8d, the substrate 12 is then folded along a second foldline 44 such that a second edge 46 of the substrate 12 is positioned adjacent the longitudinal centerline 52 and the second region 34 overlays a portion of the central region 26 to provide an absorbent composite 10 having a "c"-shaped cross-section 50.

Figure 9A:
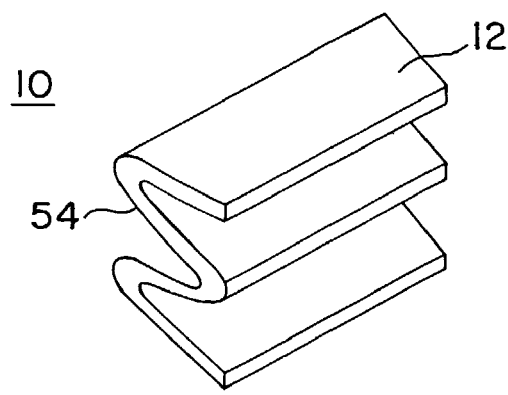
FIGS. 9a through 9c illustrate representative absorbent composites having various other cross-sectional configurations.
Figure 9B:
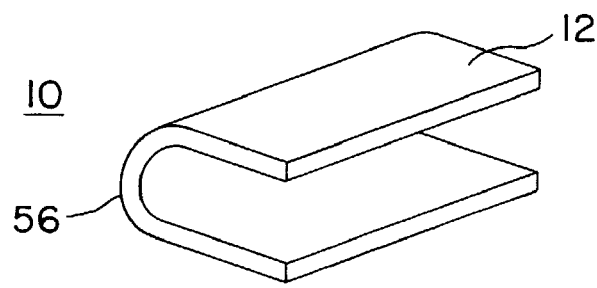
Figure 9C:
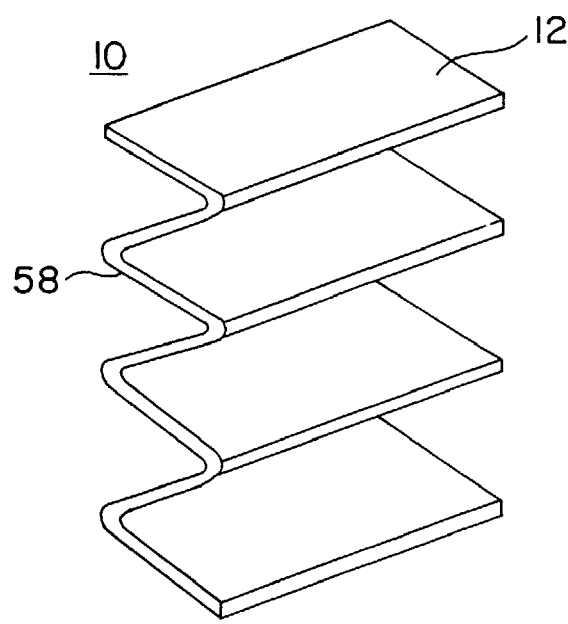

Other suitable cross-sectional configurations are illustrated in FIGS. 9a through 9c. For example, FIG. 9a depicts an absorbent composite 10 having a "sigma"-shaped cross-section 54. FIG. 9b shows an absorbent composite 10 having a "u"-shaped cross-section 56 while FIG. 9c shows an absorbent composite 10 having an "accordion"-shaped cross-section 58. Additionally, the substrate 12 may be folded in any other manner such that the resulting absorbent composite 10 includes a plurality of panels. Suitably, the substrate may be cut, slit, scored, perforated, apertured or the like to facilitate folding.

The process for making the absorbent composite 10 may optionally include the steps of cutting, embossing, bonding, pressing and/or shaping the folded substrate to impart additional fluid handling functionality and/or aesthetic properties to the absorbent composite 10. For example, the folded substrate 12 may be embossed with one of a number of discreet bond patterns. One example of a pattern is the Hansen and Pennings or "H&P" pattern as taught in U.S.

Pat. No. 3,855,046 to Hansen and Pennings. Another typical embossing pattern is the expanded Hansen and Pennings or "EHP". Other common patterns include a "Ramisch" diamond pattern with repeating diamonds and an "S" weave pattern as described in commonly assigned U.S. Pat. No. 5,964,742 to McCormack et al., which is incorporated by reference. Additional patterns include, for example, cross directional lines, machine directional lines or other extensible patterns known in the art. One such extensible pattern suitable for use in the present invention is known as "wire weave".

In one embodiment of the present invention at least a portion of a substrate having a basis weight of about 150 grams per square meter or less is coated with an absorbent adhesive composition including an absorbent binder or an absorbent in situ neutralizable binder composition and a superabsorbent material. The substrate is folded such that the absorbent adhesive composition is enclosed within the resulting absorbent composite.

In another embodiment, a multifunctional substrate having an average basis weight of about 150 grams per square meter or less includes at least a first region having a first density, and at least a second region having a density different than the first region. For example, the second region may have a density that is lower than the density of the first region. At least a portion of the first region is coated with an absorbent adhesive composition and at least a portion of the second region is uncoated with the absorbent adhesive composition. The multifunctional substrate is folded such that the uncoated lower density region overlays the coated region thereby enclosing the absorbent adhesive composition within the resulting absorbent composite.

In a further embodiment, a multifunctional substrate having an average basis weight less of about 150 grams per square meter or less includes at least one apertured region and at least one unapertured region. At least a portion of the unapertured region is coated with an absorbent adhesive composition while at least a portion of the apertured region is uncoated. The multifunctional substrate is folded such that the uncoated, apertured region overlays the coated, unapertured region thereby enclosing the absorbent adhesive composition within the resulting absorbent composite.

The absorbent composite 10 of the invention can be incorporated into any suitable absorbent article. Furthermore, the absorbent composite 10 may be positioned or oriented within the absorbent article in any manner that provides the desired fluid handling properties. The absorbent composite 10 of the invention is particularly suitable for absorbing liquids such as urine, menses, or sweat, or gases, especially malodorous gases. Examples of absorbent articles that may include an absorbent composite 10 include absorbent garments such as training pants, diapers, diaper pants, feminine hygiene products, swimwear, incontinence products, other personal care or health care garments, including medical garments, or the like and absorbent products such as wipes, tissues, underarm sweat pads and bed mats or pads. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults. As used herein the term "feminine hygiene product" includes sanitary pads and napkins, as well as tampons and interlabial feminine hygiene products.

Desirably, absorbent articles including an absorbent composite 10 of the present invention should have an average thickness of about 6.4 millimeters or less. Furthermore, the structural components of an absorbent article including an absorbent composite 10 of the present invention suitably have a thickness of between about 0.2 and about 4 millimeters (mm), or between about 0.5 and about 3.0 mm, or between about 1.0 and about 2.5 mm, as measured at 0.05 pounds square inch (psi) (0.34 kPascals), and an absorbent capacity of between about 0.1 and about 1.8 $g/cm^2$, or between about 0.5 and about 1.4 $g/cm^2$, or between about 0.7 and about 1.1 $g/cm^2$ under an applied load of 0.3 psi (2.07 kPascals). The absorbent capacity of the material can be measured according to the test method described in detail below.

Figure 10A:
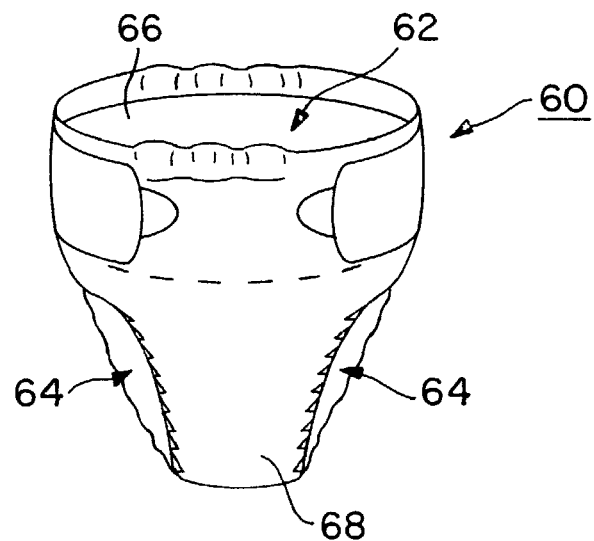
FIGS. 10a and 10b illustrate representative diapers including an absorbent composite.
Figure 10B:
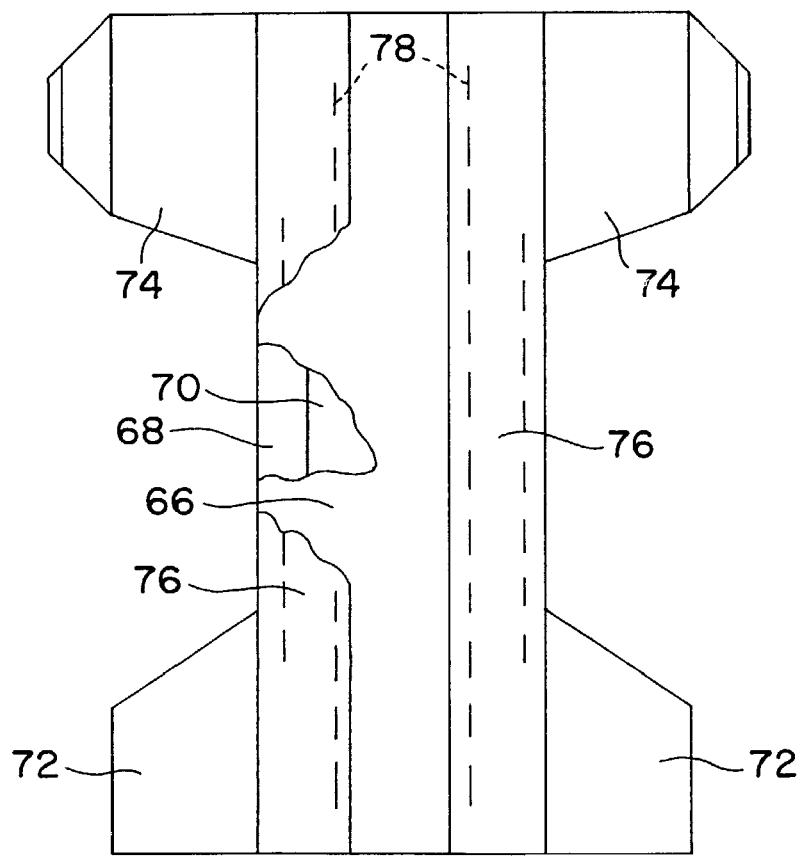

In one aspect, the absorbent composite 10 can be incorporated into an absorbent garment. For ease of explanation, the description hereafter will be in terms of the absorbent composite 10 incorporated into a diaper 60. As shown in FIG. 10a, a diaper 60 having refastenable sides in a fastened position, defines a three-dimensional configuration having a waist opening 62 and a pair of leg openings 64. Referring to FIGS. 10a and 10b, the diaper 60 includes a body-side liner 66 which is configured to contact the wearer, and an outer cover 68 opposite the body-side liner which is configured to contact the wearer's clothing. An absorbent assembly 70 is positioned or disposed between the outer cover 68 and the body-side liner 66. In one embodiment an absorbent composite 10 of the invention may be inserted into the diaper as the absorbent assembly 70.

The outer cover 68 desirably includes a material that is substantially liquid impermeable, and can be elastic, stretchable or nonstretchable. The outer cover 68 can be a single layer of liquid impermeable material, but desirably includes a multi-layered laminate structure in which at least one of the layers is liquid impermeable. For instance; the outer cover 68 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., or from National Starch and Chemical Company, Bridgewater, N.J. The liquid permeable outer layer can be any suitable material and desirably one that provides a generally cloth-like texture. One example of such a material is a 20 grams per square meter (gsm) spunbond polypropylene nonwoven web. The outer layer may also be made of those materials of which liquid permeable body-side liner 66 is made. While it is not a necessity for the outer layer to be liquid permeable, it is desired that it provides a relatively cloth-like texture to the wearer.

The inner layer of the outer cover 68 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 68 when a single layer, prevents waste material from wetting articles, such as bedsheets and clothing, as well as the wearer and care giver. A suitable liquid impermeable film for use as a liquid impermeable inner layer, or a single layer liquid impermeable outer cover 68, is a 0.2 millimeter polyethylene film commercially available from Huntsman Packaging of Newport News, Va. If the outer cover 68 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 68. A suitable breathable material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

Certain non-breathable elastic films can also be used to make the outer cover 68. Examples of suitable non-breathable films can be made of styrene-ethylene-butylene-styrene or styrene-isoprene-styrene block copolymers, KRATON polymers from Kraton Polymers of Houston, Tex., metallocene catalyzed elastomers or plastomers, and the like. Other materials suitable for making the outer cover 68 include monolithic breathable films, such as those made of polyether amide based polymers, for example PEBAX from Atofina Chemicals, Inc. of Philadelphia, Pa., and ether/ester polyurethane thermal-plastic elastomers.

The liquid permeable body-side liner 66 is illustrated as overlying the outer cover 68 and absorbent assembly 70, and may but need not have the same dimensions as the outer cover 68. The body-side liner 66 is desirably compliant, soft feeling, and non-irritating to the wearer's skin. Further, the body-side liner 66 can be less hydrophilic than the absorbent assembly 70, to present a relatively dry surface to the wearer and permit liquid to readily penetrate through its thickness.

The body-side liner 66 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body-side liner 66. For example, the body-side liner can be composed of a meltblown or spunbonded web of polyolefin fibers. The body-side liner can also be a bonded-carded web composed of natural and/or synthetic fibers. The body-side liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL N-62 available from Uniqema Inc., a division of ICI of New Castle, Del. and GLUCOPON 220UP available from Cognis Corporation of Ambler, Pa., and produced in Cincinnati, Ohio, in an active ratio of 3:1. The surfactant can be applied by any conventional means, such as spraying, printing, brush coating or the like. The surfactant can be applied to the entire body-side liner 66 or can be selectively applied to particular sections of the body-side liner, such as the medial section along the longitudinal centerline.

Non-absorbent structural components in the diaper 60 may include a pair of transversely opposed front side panels 72, and a pair of transversely opposed back side panels 74. The side panels 72, 74 may be integrally formed with the outer cover 68 and/or the body-side liner 66, or may include two or more separate elements.

Other non-absorbent structural components in the diaper 60 may include a pair of containment flaps 76 which are configured to provide a barrier to the transverse flow of any body exudates discharged from the wearer. A flap elastic member 78 may be operatively joined with each containment flap 76 in any suitable manner as is well known in the art. The elasticized containment flaps 76 define an unattached edge that assumes an upright, generally perpendicular configuration in at least a crotch region of the diaper 60 to form a seal against the wearer's body. The containment flaps 76 can be located along transversely opposed side edges of the diaper 60, and can extend longitudinally along the entire length of the training pant or may only extend partially along the length of the diaper. Suitable constructions and arrangements for the containment flaps 76 are generally well known to those skilled in the art.

In another aspect, an absorbent composite 10 of the present invention may be used to form an absorbent garment. For example, an absorbent garment may include an absorbent composite including a substrate, at least a portion of which is coated with an absorbent adhesive composition, which is folded to provide a plurality of panels at least one of which forms an outer cover of the garment.

Figure 11:
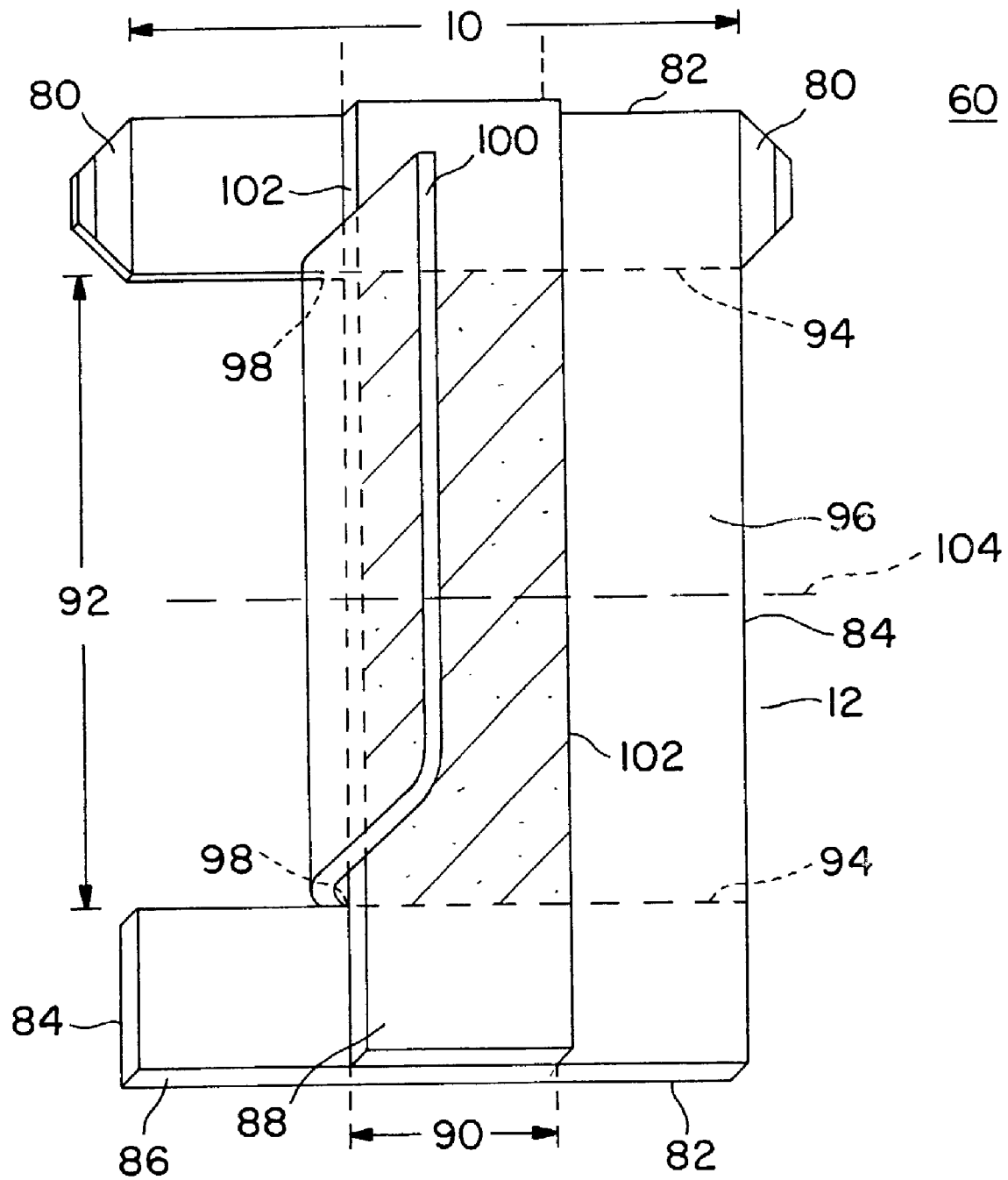
FIG. 11 is a plan view of a diaper formed from an absorbent composite.

In a specific embodiment, the absorbent composite 10 may be used to form a diaper 60. Referring to FIG. 11, a diaper 60 includes an absorbent composite 10 and a pair of fastening means 80. The absorbent composite 10 includes a substrate 12 having a pair of longitudinal ends 82 and a pair of transverse edges 84, and an absorbent adhesive composition. The substrate 12 includes a sheet of a nonwoven material 86, having a width dimension and a length dimension, such as, for example, a 20 grams per square meter (gsm) spunbond polypropylene nonwoven web, at least a portion of which is laminated to a sheet of breathable film 88 such as, for example, a microporous polymer film. Suitably, the breathable film 88 has a length dimension comparable to the length dimension of the nonwoven material and a width dimension that is smaller than the width dimension of the nonwoven material. Advantageously, the breathable film 88 is laminated to the nonwoven sheet 86 in a medial section 90 of the substrate 12. The breathable film 88 may be laminated to the nonwoven sheet 86 by any means known in the art such as, for example, heat embossing, thermal bonding, ultrasonic welding, and/or adhesive lamination.

Desirably, the absorbent adhesive composition is applied to at least a portion of the substrate 12, alternatively to at least a portion of the substrate 12 where the nonwoven sheet 86 is laminated to the breathable film 88, or to at least a central section 92 of the substrate 12 where the nonwoven sheet 86 is laminated to the breathable film 88.

The substrate 12 is slit or cut along a pair of left transverse cutting lines 94 to form a left central section 96 and along a pair of right transverse cutting lines 98 to form a right central section 100. Suitably, the transverse cutting lines 94 and 98 extend from the transverse edges 84 to a pair of transverse edges 102 of the medial section 90 of the substrate 12. The substrate 12 is then folded such that the left central section 96 and the right central section 100 overlay the medial section 90 of the substrate 12 thereby enclosing the absorbent adhesive composition within the absorbent composite 10. Although the medial section 90, the left central section 96 and the right central section 100 are illustrated in FIG. 11 as having comparable width dimensions, it should be understood that the sections may have any dimension suitable to allow the substrate 12 to be folded in a manner that encloses the absorbent adhesive composition within the absorbent composite 10.

As shown in FIG. 11, a pair of fastening means 80 may be provided along each transverse edge 84 of the substrate 12 adjacent one of the longitudinal ends 82. The fastening means 80 may be of any type known in the art such as, for example, tapes, hook and loop fasteners, buttons, snaps and the like. Suitably, the fastening means are refastenable such that the diaper 60 may be opened and closed multiple times while in use. Alternatively, the absorbent composite 10 may be folded along a transverse centerline 104 such that the longitudinal ends 82 are placed in a juxtaposed configuration and the lateral edges 84 may be sealed, fused or bonded together to form a 3-dimensional pant. Additional elements such as, for example, waist elastic positioned adjacent the longitudinal ends 82 of absorbent composite 10, leg elastics incorporated adjacent the longitudinal edges 102 of the medial section of the absorbent composite 10, or extensible side panels incorporated along the transverse edges 84 of the absorbent composite 10 adjacent the longitudinal ends 82, may be incorporated into the absorbent composite to provide better fit, comfort and leakage protection in use.

Although the diaper 60 illustrated in FIG. 11 has a generally "I"-shaped configuration it is to be understood that other configurations such as an "hour-glass" shape, "trapezoidal" shape or the like may also be achieved using other folding sequence with or without cutting the substrate to form the absorbent composite 10. Generally, any shape that may be achieved by folding and optionally cutting the substrate 12 may be used to make an absorbent garment formed from an absorbent composite of the present invention. The absorbent composite 10 may be further shaped by molding, pressing, trimming, heating or the like to achieve a desired 2- or 3-dimensional configuration. The absorbent composite 10 may also be embossed or printed to impart desired surface aesthetics.

It is to be understood that although the foregoing description has been drafted in terms of a diaper, the present invention may also be used to form similar absorbent articles such as, for example, training pants, adult incontinence products and garments, feminine hygiene garments, swimwear, and other absorbent garments.

In a further aspect, the absorbent composite 10 can be used to form a feminine hygiene product 106 without the addition of other non-absorbent structural components such as baffles or barrier layers. For example a feminine hygiene product may include an absorbent composite, a moisture-insensitive adhesive and a release strip.

Figure 12:
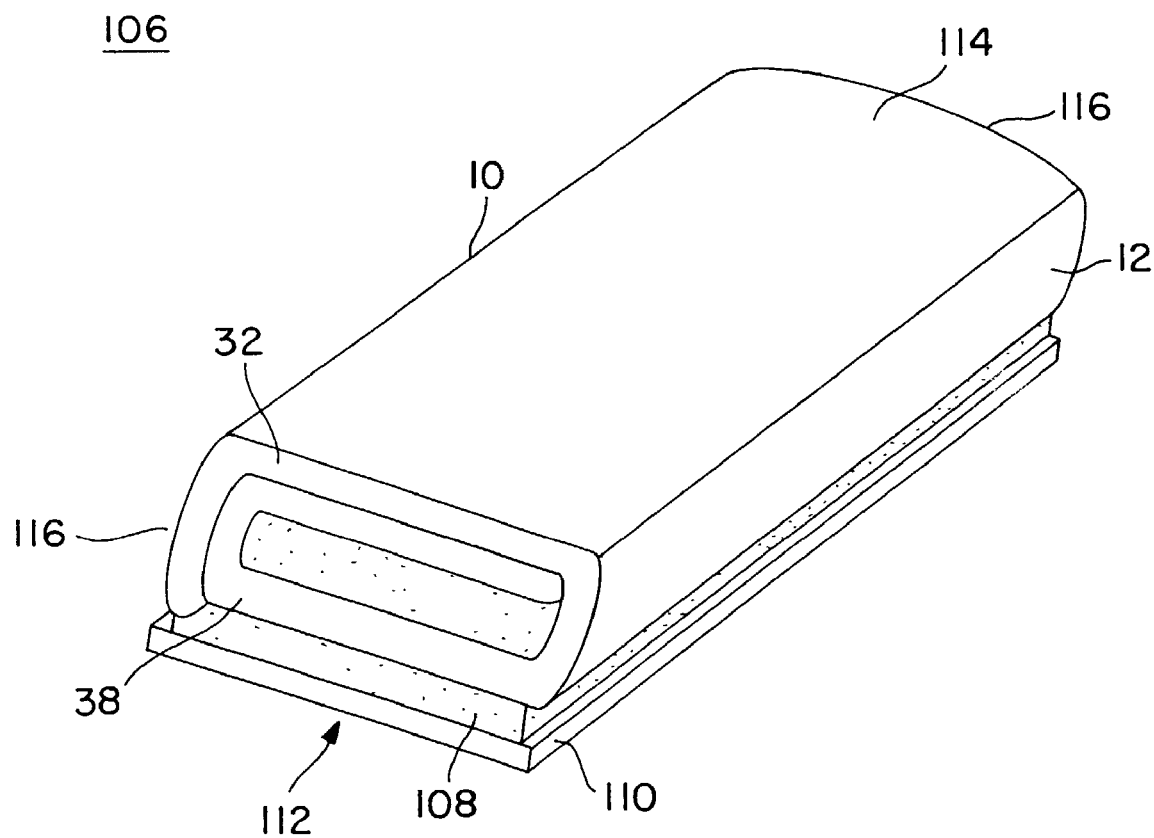
FIG. 12 is a plan view of a feminine hygiene product including an absorbent composite.

In a specific embodiment, as shown in FIG. 12, a feminine hygiene product 106 includes an absorbent composite 10, a layer of a moisture-insensitive adhesive 108, and a release strip 110. The absorbent composite 10 includes a substrate 12 and an absorbent adhesive composition. Suitably, the substrate 12 includes a body side liner material, manufactured from any of a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like, that is liquid permeable, soft and non-irritating to the wearer's skin. At least a portion of the substrate 12 is coated with the absorbent adhesive composition using any suitable application pattern and method. The substrate 12 is then folded to provide a garment-facing surface 112 and a body-facing surface 114. Desirably, the body-facing surface 114 is adjacent an uncoated portion 32 of the substrate 12. As shown, in FIG. 12, the absorbent composite 10 has an "e"-shaped cross-section 38, however, other cross-sectional configurations are also suitable. The absorbent composite 10 provides at least three fluid handling functions: the substrate 12 provides body contact functionality; and the absorbent adhesive composition provides retention and the moisture-insensitive adhesive provides barrier functionality. Optionally, a sheet of a cellulosic material (not shown) such as uncreped-through-air-dried tissue may be included in the absorbent composite 10 to provide wicking functionality. At least a portion of the garment-facing side 112 of the absorbent composite 10 is coated with a layer of moisture-insensitive adhesive 108. The adhesive may be any type known in the art that can provide a suitable garment attachment means. The layer of moisture-insensitive adhesive 108, in addition to providing a garment attachment means, also provides a means for securing the substrate 12 in a folded configuration and assists in providing barrier functionality. The release strip 110 may be any material suitable to protect the moisture-insensitive adhesive during storage of the feminine hygiene product but should be easy to remove by the consumer when the product is used. Advantageously, the longitudinally spaced ends 116 are sealed to prevent leakage of fluid and/or the particles and/or the crosslinkable binder composition from the absorbent composite 10. The ends 116 may be sealed by any means known in the art such as, for example, adhesive bonding, thermal bonding, point bonding and/or ultrasonic welding. As illustrated in FIG. 12, the feminine hygiene product 106 has a substantially rectangular configuration. However, other configurations, such as an hour glass-shape or a winged-shape that may be achieved by cutting and folding the substrate in various manners, are also suitable. Alternatively, the absorbent composite 10 may be cut, embossed, molded, pressed or the like to impart a desired 2- or 3-dimensional shape.

EXAMPLES

Example 1

An absorbent composite of the present invention was prepared as follows. A 3-inch×8-inch (about 7.6 centimeter× 20.3 centimeter) sheet of a breathable film having a basis weight of 0.04 osy (about 1.36 gsm) was placed in a juxtaposed relationship with a 6-inch×8-inch (about 15.2 centimeter×20.3 centimeter) sheet of spunbond material having a basis weight of 0.6 osy (about 20.4 gsm) such that one of the longer edges of the film sheet was positioned adjacent one of the longer edges of the spunbond sheet. The film and spunbond were laminated via heat embossing to provide a substrate including a first panel and a second panel. The first panel included the spunbond material and the second panel included the spunbond/film laminate.

The spunbond side of the second panel was hand-coated with an absorbent crosslinkable binder composition applied uniformly in a concentration of about 100 grams per square centimeter. The crosslinkable binder composition was a copolymer of 57 mole percent acrylic acid, 42 mole percent polyethylene glycol methacrylate, and 1 mole percent methacryloxypropyl trimethoxy silane. The acrylic acid portion of the copolymer was neutralized to 50 percent with sodium hydroxide solution.

The crosslinkable binder composition was prepared as follows. An initiator solution was prepared by dissolving 0.354 grams of benzoyl peroxide in 300 milliliters of ethanol. A monomer solution was prepared by mixing 24.15 grams of acrylic acid (24 mass percent), 73.5 grams of poly(ethylene glycol) methyl ether methacrylate (74 mass percent) and 1.46 grams of 3-(trimethoxysilyl)propyl methacrylate (2 mass percent) in 250 milliliters of ethanol. The initiator solution was heated in a jacketed reactor to 75 degrees Celsius with stirring. The monomer solution was added dropwise to the initiator solution to form a polymerization solution. The polymerization solution was stirred and heated at 75 degrees Celsius for approximately 2 hours after which a solution of 0.096 grams azobisisobutyronitrile (AIBN), dissolved in 30 milliliters of ethanol, was added. The polymerization solution was stirred and heated at 75 degrees Celsius for another hour at which time a second solution of 0.096 grams AIBN in ethanol was added to the polymerization solution. The polymerization solution was stirred and heated at 75 degrees Celsius for an additional hour after which a third addition of 0.096 grams AIBN in ethanol was made. Stirring and heating of the polymerization solution continued at 75 degrees Celsius for an additional time to reach a total reaction time of about 7 hours. The reactor was cooled to 20 degrees Celsius and the resulting polymer solution was stirred in a nitrogen atmosphere overnight to provide a binder polymer designated binder polymer 1a. A portion of the polymer solution was dried for 16 hours at room temperature to create a sticky, crosslinked water-absorbent film. The polymer concentration of the polymer solution was 16.2 percent by weight.

A portion of the polymer solution was treated with sodium hydroxide solution to neutralize a portion (50 percent) of the acrylic acid units in the binder polymer 1a in order to increase the absorbency of the crosslinked film generated by drying the polymer solution. The neutralization was done by adding 5.25 grams of 48.5 percent sodium hydroxide solution to 236 grams of polymer solution (16.2 percent polymer) and stirring at room temperature for 5 minutes.

The first panel of the substrate was folded over the second panel thereby enclosing the absorbent crosslinkable binder composition between the two panels. The folded substrate was placed on the bottom plate of a flat Carver press, Model 25-15HC (Catalog No. 3977) available from Fred S. Carver, Inc., Wabash, Ind. Shims having a thickness of 0.9 millimeters were also placed on the bottom plate of the Carver press to provide gap-stops. Accordingly, when the top and bottom plates of the Carver press were brought together the top plate contacted the shims and a 0.9-millimeter gap was formed between the two plates. The folded substrate was compressed for 10 seconds with a force of 10,000 pounds (44,450 Newtons) at room temperature (approximately 73° F. or 23° C.) to provide an absorbent composite of the present invention having a "u"-shaped cross-section and a thickness of about 0.9 millimeters.

Example 2

An absorbent composite of the present invention was prepared as in Example 1 except prior to folding the first panel over the second panel a piece of tissue web was placed over the coated portion of the second panel. The tissue web was prepared using the Uncreped Through-Air Dried (UC-TAD) process as described in U.S. Pat. Nos. 5,656,132 and 5,932,068 to Farrington, Jr., et al., and had a basis weight of 50 grams per square meter. The first panel was then folded over the second panel thereby enclosing the absorbent crosslinkable binder composition and the UCTAD sheet between the two panels. After compression, the resulting absorbent composite had a "u"-shaped cross-section and a thickness of about 1.4 millimeters.

Example 3

An absorbent composite of the present invention was prepared as follows. A 3-inch×8-inch (about 7.6 centimeter× 20.3 centimeter) sheet of a breathable film having a basis weight of 0.04 osy (about 1.36 gsm) was placed in a juxtaposed relationship with a 9-inch×8-inch (about 22.9 centimeter×20.3 centimeter) sheet of spunbond material having a basis weight of 0.6 osy (about 20.4 gsm) such that the film sheet was positioned adjacent a medial 3-inch×8-inch (about 7.6 centimeter×20.3 centimeter) section of the spunbond sheet. The film and spunbond were laminated via heat embossing to provide a substrate including a first panel, a second panel, and a third panel having approximately equal dimensions. The first panel included spunbond material, the second panel included the spunbond/film laminate and the third panel included spunbond material.

The second panel was coated with the absorbent crosslinkable binder composition as disclosed in Example 1. The first panel was sprayed with a surfactant mixture including AHCOVEL N-62 available from Uniqema Inc., a division of ICI of New Castle, Del., U.S.A. and GLUCOPON 220UP available from Cognis Corporation of Ambler, Pa., and produced in Cincinnati, Ohio, in an active ratio of 3:1. The surfactant was applied at a concentration of about 0.45 weight percent based on the total weight of surfactant and the spunbond material of the first panel.

The first panel was folded over the second panel thereby enclosing the absorbent crosslinkable binder composition and the surfactant between the first and second panels. The third panel was then folded over the first panel and the folded substrate was placed on the bottom plate of a Carver press. Shims having a thickness of 1.2 millimeters were also placed on the bottom plate of the Carver press to provide gap-stops. The folded substrate was compressed as in Example 1 to provide an absorbent composite of the present invention having an "e"-shaped cross-section and a thickness of about 1.2 millimeters.

Example 4

A feminine hygiene product of the present invention was formed using the absorbent composite of Example 1 as follows. Three strips of a moisture-insensitive adhesive were applied to the film side of the second panel at a concentration of about 5 to about 10 grams per square centimeter, and were covered by an adhesive releasable paper. The moisture-insensitive adhesive was NS-34-5561 available from National Starch and Chemical Company of Bridgewater, N.J. The absorbent composite was die-cut into a dumbbell shape to form a feminine hygiene product.

Example 5

A piece of surge material made according to U.S. Pat. No. 5,364,382 to Latimer et al., manufactured by Kimberly-Clark was coated with a mixture of 8.7 grams superabsorbent material and 19.3 grams of a crosslinkable binder composition in 15 percent w/w ethanol. The surge material had a basis weight of 1.5 osy (about 50.9 gsm). The superabsorbent material was FAVOR SXM 9543, available from Stockhausen Inc., located in Greensboro, S.C. The crosslinkable binder composition was a copolymer of 70 mole percent acrylic acid, 29 mole percent polyethylene glycol methacrylate, and 1 mole percent methacryloxypropyl trimethoxy silane. The acrylic acid portion of the copolymer was neutralized to 70 percent with sodium hydroxide solution.

The coating was applied with a spatula onto the medial 3-inch×12-inch (about 7.6 centimeter×30.5 centimeter) region of a 9-inch×12-inch (about 22.9 centimeter×30.5 centimeter) sheet of surge material. The coated surge material was placed in a fume hood at room temperature to evaporate the ethanol. After the ethanol had evaporated, the surge material was folded as illustrated in FIGS. 6b through 6d to provide an absorbent composite of the present invention having an "e"-shaped cross-section that provides both fluid intake and retention functionality.

Example 6

An absorbent composite of the present invention was prepared as in Example 5 except one of the side sections of the surge material was folded over the coated medial section of the surge material prior to evaporating the ethanol. The ethanol was then evaporated in order to set the binder composition and to adhere the first side section to the absorbent crosslinkable binder composition to provide more intimate contact between the coated and uncoated sections. The second side section was then folded over the first side section to provide an absorbent composite of the present invention having an "e"-shaped cross-section.

Example 7

An absorbent composite including a multifunctional substrate was prepared as follows. A multifunctional substrate was prepared by placing a first 3-inch×12-inch (about 7.6 centimeter×30.5 centimeter) section of a 9-inch×12-inch (about 22.9 centimeter×30.5 centimeter) sheet of surge material as in Example 5 on the bottom plate of a Carver press. Shims having a thickness of 0.5 millimeters were also placed on the bottom plate of the Carver press to provide gap-stops. The top and bottom plates of the Carver press were heated to about 220° F. (about 105° C.). The first section of the surge material was compressed between the top and bottom plates for 60 seconds with a force of 10,000 pounds (44,450 Newtons) to increase the density of the first section of the surge material. The compressed first section of the surge material had a density approximately twice that of the uncompressed remainder of the sheet.

A coating of an absorbent crosslinkable binder composition and superabsorbent material as in Example 5 was then applied to a medial 3-inch×12-inch (about 7.6 centimeter×30.5 centimeter) section of the surge material. The surge material was then folded as illustrated in FIGS. 6b through 6d such that the densified first section of the surge material was positioned adjacent the coated medial section of the surge material and the undensified, uncoated section of the surge material was positioned adjacent the densified first section of the surge material to form an absorbent composite having an "e"-shaped cross-section. The resulting absorbent composite provides intake, distribution, and retention functionality.

Example 8

An absorbent composite including a multifunctional substrate was prepared as follows. A multifunctional substrate was prepared as in Example 7. Similar to Example 6, a medial section of the surge material was coated with the absorbent cross-linkable binder composition and superabsorbent material of Example 5 and the densified section of the surge material was folded over the coated medial section prior to evaporating the ethanol. After the ethanol was evaporated the undensified section of the surge material was folded over the densified section of the surge material to form an absorbent composite of the present invention having an "e"-shaped cross-section.

Test Method for Determining Absorbent Capacity

Centrifuge Retention Capacity: The Centrifuge Retention Capacity (CRC) is a test which measures the amount in grams of a test liquid, such as water or a 0.9 weight percent solution of sodium chloride in distilled water, that a gram of a material can absorb or immobilize in a single time interval, or a series of time intervals, after being subjected to a centrifugal force for a period of time.

Stock teabag material is cut into a 3-inch (about 7.6 centimeters) by 5-inch (about 12.7 centimeters) rectangle and folded in half to form a 2.5-inch (about 6.4 centimeters) by 3-inch (about 7.6 centimeters) rectangle with the sealable face inward. Two of the three open sides are heat sealed with the inside edge of the seal about 0.25 inch (about 0.64 centimeter) from the edge. About 0.2 gram of sample material (or a 1-inch by 1-inch square piece of composite) is placed into a preweighed teabag, and the open end of the teabag is heat sealed. The teabag is submerged in a pan of test liquid for a time interval, removed, allowed to drain on a wire mesh at about a 45 degree angle for about 2 minutes, centrifuged for about 3 minutes at 290 times the gravitational force and then weighed. If a series of time intervals is to be run, the sample is returned to the test liquid until the next time interval. After each time interval, the teabag is again allowed to drain on the wire mesh for about 2 minutes, again centrifuged for about 3 minutes at 290 times the gravitational force, and then weighed again. After the final time interval, the teabag is then allowed to dry and then weighed again. A blank test is also run by centrifuging under similar conditions an empty teabag which had also been placed in the test liquid. The weight of the test liquid retained per gram of dry sample material after centrifuging is calculated from the data obtained, and this is expressed as the Centrifuge Retention Capacity value in terms of grams of test liquid retained per gram of dry sample material.

Test Method for Determining Absorbency Under Load for Composites (AULC)

The Absorbency Under Load for Composites (AULC) is a test which measures the ability of an absorbent material to absorb a liquid (such as a 0.9 weight percent aqueous solution of sodium chloride) while under an applied load or restraining force. The AULC method provides a slight positive head of fluid for the absorbent material, which is allowed to swell under a restraining load. The material is drained under vacuum at the end of the test.

The AULC test cup is cylindrical with a height of at least 1.75 inches; the inner diameter describes a cylinder, the base of which has an area of 4.37 in$^2$. The bottom of the test cup is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder. A spacer weighing about 60 grams and having a circular diameter of about 2.36 inches is made to fit within the AULC test cup without binding. The spacer is formed with multiple cylinder holes of about 9 mm diameter, providing an open area of about 52 percent. A 100 mesh screen is adhered to the bottom of the spacer in a similar manner as the mesh which is attached to the bottom of the test cup or other suitable method. Weights are sized to fit on top of the spacer. The first weight should apply a load of 600 grams (in combination with the spacer), and the second weight, in combination with the first weight and the spacer disc, should apply a load of 1800 grams.

Additional equipment required includes a vacuum trap for liquid that is suctioned out of the composite material at the end of the test, shallow dishes such as Petri dishes or plastic weighing boats suitable for holding an excess amount of liquid than will be imbibed by the sample, and a thin mesh screen with a thickness between 0.3 mm and 0.75 mm and a mesh size of about 1.2 mm. The vacuum trap is adapted to apply vacuum to an area matching the dimensions of the bottom of the AULC testing cup (for example, a larger vacuum area may be selectively screened with a relatively impermeable material except in an area matching the dimensions of the bottom of the AULC cup). The vacuum applied is about 27 inches of mercury.

Composite samples are cut to fit inside the AULC testing cup. Airlaid or nonwoven-based materials are cut into circles 2.35 inches in diameter. Airformed samples are cut or formed into circles, each with a diameter of 2.312 inches.

To carry out the test, test cup and spacer should be clean and dry. The test cup and spacer to be used in each trial should be weighed together (Measurement 1), and the mass recorded. The specimen is placed in the sample cup and the spacer is placed on top of the sample in the cup. The assembly is then weighed (Measurement 2), and the mass is recorded. The appropriate amount of weight is placed atop the spacer, if required. The spacer alone applies a force of 0.03 pounds per square inch of area (psia; the disc and first weight, with a net mass of 600 grams, apply a force of 0.3 psi, and the disc and both weights together, having a net mass of 1800 grams, apply a force of 0.9 psi).

The cup holding the specimen is placed in a pool of excess fluid in the shallow dish on top of the mesh screen and a one hour timer is started immediately. The level of fluid in the dish is maintained between about 1 mm and 2 mm depth. Following one hour, the specimen is removed from the fluid bath. Any fluid that may have accumulated atop the specimen should be poured off without displacing any weights atop the spacer disc. The specimen assembly is then placed on the vacuum box, with any weights still in place. Vacuum is applied to the sample for 30 seconds.

Any weights atop the spacer are then removed from the assembly and the assembly is weighed again (Measurement 3). The mass is recorded.

The dry weight of the specimen is calculated by subtracting Measurement 1 from Measurement 2. The amount of fluid absorbed by the specimen is calculated by subtracting Measurement 2 from Measurement 3. The absorbency under load of the composite material is calculated as the amount of fluid absorbed divided by the dry weight of the specimen.

At least three specimens of each sample should be measured, and the absorbency under load values should be averaged to obtain an overall absorbency under load for the composite sample.

Test for Determining Tensile Strength

The tensile strength can be measured using the Strip Tensile Test Method described in U.S. Statutory Invention Registration No. H1,969 issued to Fell on Jun. 5, 2001.

Test for Determining Thickness

All measurements of composite thickness were done at a pressure of 0.05 psi (0.34 kPascals) with a Mitutoyo Digimatic Indicator (Type IDF 150E), available from Mitutoyo American Corporation of Aurora, Ill., equipped with a "foot" composed of a plastic disk having a diameter of 3 inches (7.6 centimeters) and a weight of 78.5 grams. The instrument is zeroed with the foot in contact with the baseplate. A sample is placed on the baseplate and the foot is lowered onto the sample until a load of 0.05 psi (0.34 kPascals) is applied. The thickness of the sample is then measured to the nearest 0.01 millimeter.

Test Method for Determining Stiffness

A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester, Model 4171-E, manufactured by Teledyne Gurley, a business having offices in Troy, N.Y. For purposes of the present invention, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. An absorbent composite comprising:
   a substrate; and
   an absorbent crosslinkable binder composition, comprising an alkoxysilane functionality which, upon exposure to water, forms a silanol functional group which condenses to form a crosslinked polymer,
   wherein at least a portion of the substrate is coated with the absorbent crosslinkable binder composition, and the substrate is folded to provide a plurality of panels.

2. The absorbent composite of claim 1, wherein at least a first panel of the substrate provides a first fluid handling function and at least a second panel of the substrate provides a second fluid handling function.

3. The absorbent composite of claim 2, wherein the fluid handing functions are selected from the group consisting of barrier function, body contact, distribution, feces containment, feces modification, intake, lock-up, menses containment, menses modification, odor control, retention, and skin treatment.

4. The absorbent composite of claim 1, wherein the substrate has a basis weight of about 150 grams per square meter or less.

5. The absorbent composite of claim 1, wherein the substrate has a fluid centrifuge retention capacity of about 10 grams 0.9 weight percent saline per gram substrate or less.

6. The absorbent composite of claim 1, wherein the substrate has a peak tensile strength under load of about 50 grams per centimeter width or more.

7. The absorbent composite of claim 1, wherein the substrate comprises a material selected from the group consisting of nonwoven webs, woven webs, knitted fabrics, cellulosic tissue sheets, plastic films, foams, stranded composites, elastomer net composites and combinations thereof.

8. The absorbent composite of claim 1, wherein the absorbent crosslinkable binder composition includes a soluble polymer selected from the group consisting of hydrophilic polymers, a blend of hydrophilic polymers containing hydrophilic agents, and a blend of hydrophobic polymers including hydrophilic agents.

9. The absorbent composite of claim 8, wherein the absorbent crosslinkable binder composition comprises an alkoxysilane grafted poly(ethylene oxide).

10. The absorbent composite of claim 8, wherein the absorbent crosslinkable binder composition has a glass transition temperature of 30 degrees Celsius or lower.

11. The absorbent composite of claim 8, wherein the absorbent crosslinkable binder composition comprises an acrylic acid copolymer selected from the group consisting of acrylic acid and long chain, hydrophilic acrylate esters, acrylic acid and long chain, hydrophilic methacrylate esters, and acrylic acid salts and long chain, hydrophilic methacrylate esters.

12. The absorbent composite of claim 1, wherein the absorbent composite has a cross-sectional configuration selected from the group consisting of an "e"-shape, a "z"-shape, a "c"-shape, a sigma-shape, a "u"-shape and an accordion-shape.

13. The absorbent composite of claim 1, wherein at least a portion of the substrate is uncoated with the absorbent crosslinkable binder composition.

14. The absorbent composite of claim 13, wherein the substrate is folded such that the uncoated portion overlays the coated portion of the substrate thereby enclosing the absorbent crosslinkable binder composition within the absorbent composite.

15. The absorbent composite of claim 1, wherein at least a portion of the substrate is treated with a fluid modifying material.

16. The absorbent composite of claim 1, wherein at least a portion of the substrate is treated with a menses-modifying material.

17. The absorbent composite of claim 1, wherein at least a portion of the substrate is coated with a moisture-insensitive adhesive.

18. The absorbent composite of claim 1, further comprising a layer of a material that provides at least one fluid handling function.

19. A disposable garment comprising:
the absorbent composite of claim 1,
wherein at least a portion of the substrate forms at least a portion of an outer cover of the garment.

20. The garment of claim 19, wherein at least a portion of the substrata is liquid permeable.

21. A feminine hygiene product comprising:
the absorbent composite of claim 1;
a garment attachment adhesive; and
a release strip.

22. The feminine hygiene product of claim 21, wherein the substrate comprises an apertured film.

23. The feminine hygiene product of claim 22, wherein at least a portion of the apertured film is treated with a fluid modifying material.

24. The feminine hygiene product of claim 21, further comprising a cellulosic tissue sheet positioned proximate to, and in contact with, the absorbent adhesive composition.

25. The feminine hygiene product of claim 21, wherein the garment attachment adhesive further secures the absorbent composite in a folded configuration.

26. An absorbent composite comprising:
a multi-functional substrate having an avenge basis weight of about 150 grams per square meter or less; and
an absorbent crosslinkable binder composition comprising an alkoxysilane functionality which, upon exposure to water, forms a silanol functional group which condenses to form a crosslinked polymer,
wherein at least a portion of the multi-functional substrate is coated with the absorbent crosslinkable binder composition, and the multi-functional substrate is folded to provide a plurality of panels.

27. The absorbent composite of claim 26, wherein the multi-functional substrate includes at least two regions having different densities.

28. The absorbent composite of claim 27, wherein at least a portion of at least a first region of the multi-functional substrate, having a first density, is coated with the absorbent crosslinkable binder composition and at least a portion of at least a second region of the multi-functional substrate, having a second density, is uncoated with the absorbent crosslinkable binder composition.

29. The absorbent composite of claim 28, wherein the multi-functional substrate is folded such that the absorbent crosslinkable binder composition is enclosed within the absorbent composite.

30. The absorbent composite of claim 26, wherein the multi-functional substrate includes at least one apertured region and at least one unapertured region.

31. A process for making an absorbent composite comprising:
providing a substrate;
applying an absorbent crosslinkable binder composition comprising an alkoxysilane functionality which, upon exposure to water, forms a silanol functional group which condenses to fain a crosslinked polymer to at least a portion of the substrate; and
folding the substrate upon itself to provide a plurality of panels.

32. The process of claim 31, further comprising shaping the absorbent composite.

33. The absorbent composite of claim 1, wherein the absorbent crosslinkable binder composition comprises:
a monoethylenically unsaturated polymer selected from the group consisting of carboxylic acid, carboxylic acid salts, sulphonic acid, sulphonic acid salts, phosphoric acid and phosphoric acid salts; and
an acrylate or methacrylate ester that comprises an alkoxysilane functionality.

34. The absorbent composite of claim 33, wherein the monoethylenically unsaturated polymer comprises a monomer selected from the group consisting of carboxyl group-containing monomers, carboxylic acid anhydride group-containing monomers, carboxylic acid salt-containing monomers, sulfonic acid group-containing monomers, and amide group-containing monomers.

35. The absorbent composite of claim 33, wherein the acrylate or methacrylate ester comprises a monomer containing a trialkoxysilane functional group.

36. The absorbent composite of claim 35, wherein the monomer comprises at least one of a group consisting of methacryloxypropyl trimethoxy silane, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy) silane.

37. An absorbent composite comprising:
a substrate; and
an absorbent crosslinkable binder composition comprising an alkoxysilane grafted poly(ethylene oxide),
wherein at least a portion of the substrate is coated with the absorbent crosslinkable binder composition, and the substrate is folded to provide a plurality of panels.

38. The absorbent composite of claim 37, wherein at least a first panel of the substrate provides a first fluid handling function and at least a second panel of the substrate provides a second fluid handling function.

39. The absorbent composite of claim 38, wherein the fluid handling functions are selected from the group consisting of barrier function, body contact, distribution, feces containment, feces modification, intake, lock-up, menses containment, menses modification, odor control, retention, and skin treatment.

40. The absorbent composite of claim 37, wherein the substrate has a fluid centrifuge retention capacity of about 10 grams 0.9 weight percent saline per gram substrate or less.

41. The absorbent composite of claim 37, wherein the alkoxysilane comprises methacryloxypropyl trimethoxy silane.

42. The absorbent composite of claim 37, wherein the alkoxysilane-grafted poly(ethylene oxide) comprises a monomer containing trialkoxysilane functional group.

43. The absorbent composite of claim 42, wherein the monomer comprises an ethylenically unsaturated monomer of an acrylate or a methacrylate.

44. The absorbent composite of claim 37, wherein the absorbent crosslinkable binder has a glass transition temperature of 30 degrees Celsius or lower.

45. The absorbent composite of claim 37, wherein the absorbent composite has a cross-sectional configuration selected from the group consisting of an "e"-shape, a "z"-shape, a "c"-shape, a sigma-shape, a "u"-shape and an accordion-shape.

46. The absorbent composite of claim 37, wherein at least a portion of the substrate is uncoated with the absorbent crosslinkable binder composition.

47. The absorbent composite of claim 46, wherein the substrate is folded such that the uncoated portion overlays the coated portion of the substrate thereby enclosing the absorbent crosslinkable binder composition within the absorbent composite.

48. The absorbent composite of claim 37, wherein at least a portion of the substrate is treated with a fluid modifying material.

49. The absorbent composite of claim 37, further comprising a layer of material tat provides at least one fluid handling function.

* * * * *